US006218364B1

(12) United States Patent
Harbeson et al.

(10) Patent No.: US 6,218,364 B1
(45) Date of Patent: Apr. 17, 2001

(54) FLUORINATED NEUROKININ A ANTAGONISTS

(76) Inventors: Scott L. Harbeson, 1000 Windsor St., Cincinnati, OH (US) 45206; James R. McCarthy, 6448 Foxview Pl., West Chester, OH (US) 45069

( * ) Notice: Subject to any disclaimer, the term of this patent is extended or adjusted under 35 U.S.C. 154(b) by 0 days.

(21) Appl. No.: 08/638,407

(22) Filed: Apr. 26, 1996

Related U.S. Application Data

(63) Continuation of application No. 08/282,341, filed on Jul. 29, 1994, which is a continuation of application No. 08/033,987, filed on Mar. 19, 1993, now abandoned, which is a continuation of application No. 07/709,092, filed on May 31, 1991, now abandoned, which is a continuation-in-part of application No. 07/686,593, filed on Apr. 17, 1991, now abandoned, which is a continuation-in-part of application No. 07/356,031, filed on May 23, 1989, now abandoned, which is a continuation-in-part of application No. 07/315,202, filed on Feb. 24, 1989, now abandoned, which is a continuation of application No. 07/208,926, filed on Jun. 20, 1988, now abandoned.

(51) Int. Cl.$^7$ .................................................. A61K 38/00

(52) U.S. Cl. ............................... 514/16; 514/16; 514/15; 514/2; 514/803; 530/329; 530/328; 530/323; 530/332; 930/31; 930/30; 930/10; 930/220

(58) Field of Search .................................. 514/16, 15, 2, 514/803; 530/329, 328, 323, 332; 930/31, 30, 10, 320, DIG. 790

(56) References Cited

U.S. PATENT DOCUMENTS

| | | | |
|---|---|---|---|
| 4,242,256 | 12/1980 | Sharpe et al. | 530/328 |
| 4,439,360 | * 3/1984 | Verdini et al. | 530/329 |
| 4,609,643 | 9/1986 | Szelke et al. | 514/16 |
| 4,638,047 | 1/1987 | Szelke et al. | 530/328 |
| 4,665,157 | 5/1987 | Wright et al. | 530/328 |
| 4,680,283 | 7/1987 | Veber et al. | 514/17 |
| 4,742,156 | 5/1988 | Wright et al. | 530/328 |
| 5,084,555 | 1/1992 | Coy et al. | 530/328 |
| 5,236,921 | 8/1993 | Emonds-Alt | 514/252 |
| 5,317,020 | 5/1994 | Emonds-Alt | 514/255 |

FOREIGN PATENT DOCUMENTS

| | | |
|---|---|---|
| 2016355 | 11/1990 | (CA) . |
| 2010246 | 6/1983 | (DE) . |
| 0109142 | * 5/1984 | (EP) . |
| 0176436 | 4/1986 | (EP) . |
| 0219258 | 4/1987 | (EP) . |
| 0401177 | 5/1990 | (EP) . |
| 0394989 | 10/1990 | (EP) . |
| 0401507 | 12/1990 | (EP) . |
| 0428434 | 5/1991 | (EP) . |
| 9003980 | 4/1990 | (WO) . |
| 9109844 | 7/1991 | (WO) . |

OTHER PUBLICATIONS

Dutta, A.S.,Drugs of the Future, vol. 12(8), 781–792 (1987).
Coy, D.H., et al., The J. of Biol. Chem., vol. 263(11), 5056–5060 (1988).
Cowan, A., et al.,Peptides in Health and Disease, Italy, Oct. 13–16, 1987. Trends in Pharm. Sci., 9(1): 1–3, (Jan. 1988).
Regoli, Chem Abst 107: 109366C (1987), Int.Congr.Ser.–Excerpta Med. 731, 85–95 (1987).
Regoli, et al.,Chem Abst 107: 1525q, (1987) (5th Annu. Wash.Spring Symp.Health Sci. J.), 501–11(1986).
Hashimoto, Chem Abst 107:211967m, (1987), Chem. Pharm.Bull. 35(8), 3442–6(1987).
Hashimoto, et al., Chem Abst 108:32646e, Jpn. J. Pharmacology, 45(4), 570–3 (1987).
Ewenson, et al., Chem Abst 106102664u (1985),, Proc. 9th Am. Pept. Symp.,639–42(1987).
Cox, et al., Chem Abst 94:31068y (1981), J.Chem.Soc., Chem. Commun. 17, 800–2 (1980).
Buck, et al., Neuroscience Abst. 14: 144 (1988), 18th Ann. Meeting for the Soc.for Neuroscience, Nov. 12–18 (1988).
Buck, et al., Chem Abst 109(11):86429a (1988), Life Sci., 42(26), 2701–8 (1988).
Rovero, et al., Chem Abst 111(13): 109167w, Peptides 10(3), 593–5 (1989).
Rovero, et al., Chem Abst 111(9):71117q (1989), Neuropeptides 13(4), 263–70 (1989).
Hashimoto, et al., Chem. Abst 107:21 (1987) 237277n.
Drapeau, et al., Chem Abst 107(19) 168939q (1987), Neuropeptides 10(1), 43–54 (1987).
Osakada, et al, Chem Abst 104(17):142380p, Eur.J.Pharmacol. 120(2), 201–8 (1986).
Drapeau, et al., Chem. Abst 111:9 (1988) 71105j.
Bristow, et al., Br. J. Pharmc 90:211–217 (1987).
Holladay et al., Tetrahedron Letters 24:41, 4401–04 (1983).
Sasaki et al., Peptides 8, 119–121 (1987).
TenBrink, et al., J. Org. Chem. 52, 418–422 (1987).
Buck et al., Science 226, 987–989 (1984).
Spatola et al., Tetrahedron 443(3):821–33 (1988).
Chorev, et al., Int. J. Peptide Protein Res. 21:258–68 (1983).
Gisin. Helvetica Chimica Acta 56(5): 1476–82 (1973).
Sandberg, et al., Proc. Eur. Pept. Symp., 18th 369–372 (1984).
Mazrahi, et al., Eur. J. Pharmacol. 118: 1–2, 25–36 (1985).
Harbeson et al., Peptides: Chemistry, Structures & Biology, Proceedings of the 11th American Peptides Symposium, Jul. 9–14, 1989.
Reifenrath, et al., J. Med. Chem. 23:985–90 (1980).
Gao, et al., J. Med. Chem. 33:39–44 (1990).
Steinman, J. Med. Chem. 16(12): 1354–60 (1973).

(List continued on next page.)

Primary Examiner—Ponnathapura Achutamurthy
Assistant Examiner—T. D. Wessendorf

(57) ABSTRACT

Peptide derivatives which are antagonists of neurokinin A. The derivatives have a modified peptide bond having a reduced amide and a fluorinated alkyl attached to the nitrogen atom of the modified peptide bond. For example, Asp-Ser-Phe-Val-Gly-LeuΨ[CH$_2$N(CH$_2$CF$_3$)]Leu(NH$_2$).

12 Claims, No Drawings

OTHER PUBLICATIONS

Barnes, Lancet 242–244 (Feb. 1, 1986).
Payan, et al., Am. Rev. Respir. Dis 136:539–34 (1987).
Devillier, et al., Inflammatory Diseases, vol. 314(20): 1323.
Dubreuil, et al., Drug Design and Delivery 2, 49–54 (1987).
Aumelas, et al., Int. J. Peptide Protein Res. 30:596–604 (1987).
Rovero, et al., Peptides 11:619–20 (1990).
Martinez, et al., J. Med. Chem. 28: 1874–79 (1985).
Sasaki, et al., J. Med. Chem. 30: 1162–66 (1987).
Morensen and Boyd, Organic Chemistry, 3rd edition, Chapter 3, pp. 79–82 (1974).
The Merck Manual of Diagnosis and Therapy, 11th edition, 1076–1078 (1966).
Rosell, Subs. P. Metab. Biol. Actions (Proc Symp) Mtg in 1984, 95–97 (1985).
Abu Shanab, et al., Biochem Soc. Trans. 17(4), 731–2 (1989).
Harbeson, et al., J. of Cellular Biochemistry Supplement 14C, p. 242, (CK305) 1990.
Snider, et al., Chemistry & Industry, Nov. 4, 1991.
Logan, et al., Annual Reports in Medicinal Chemistry 26, Chapter 5, p. 43.
Dion, et al., Life Sciences 41, 2269–2278 (1987).
McLean, et al., Biochimica Et Biophysica Acta, vol. 1024, 1–4 (1990).
Swistok, et al., Tetrahedron Letters, vol. 30(8): 5045–5048 (1989).
The Merck Manual of Diagnosis and Therapy, 11th Edition, p. 1076–1078 (1966).
Rosell, "Tachykinis and tachykinin antagonists", Subs. P. Metab. Biol. Actions (Proc Symp Meeting in 1984), pp. 95–97 (1985).
Abu Shanab et al., "Biological activity of some synthetic analogues of neurokinin A on tracheal smooth muscle from guinea–pig", Biochem Soc. Trans. 17(4), 731–2 (1989).
Drapeau, et al., Peptides: Chemistry and Biology, Tenth American Peptide Symposium, St. Louis, MO, May 25–28, 1987. Marshal, G.R. (ed). ESCOM Science Publishers: Leiden, Netherlands pp. 497–99 (1988).
Swistok, et al., Tetrahedron Letters, 30(8):5045–5048 (1989).
Rovero, P., et al., *Peptides 10*: 593–95 (1989).
Rovero, P., et al., *Neuropeptides 13*: 263–70 (1989).
Drapeau, G., et al., *Neuropeptides 10*: 43–54 (1987).
Harbeson, Scott, et al., Peptide, Chemistry, Structure and Biology, Proceedings of the Eleventh American Peptide Symposium, Jul. 9–14, 1989.
Osakada, F., et al., *Eur. J. Pharm. 120*: 201–208 (1986).
Buck, S. H. et al., Life Sciences 42: 2701–08 (1988).
Dutta, Anand S., Correlates in Pharmacostructures, pp. 781–792.
Ewenson, A., Chem Abstracts, 106, 102,664u (1987).
Coy, D. H. et al., *J. of Biol. Chem.*, 162(11): 5056–5060 (1988).
Cowan, A., ed., *Trends in Pharm. Sci. 9*(1): 1–3 (1988).
Hashimoto, T. et al., Chem Abstracts, 108, 32646 (1988).
Chem. Abstracts. 107,40346b (1987).
Chem. Abstracts. 107, 211967m (1987).
Regoli, D., et al., Chem Abstracts 107, 1525q (1987).
Regoli, D., Chem Abstracts 107, 109366c (1987).
Cox, M. T. et al., Chem Abstracts, 94,31068y (1981).
Buck, S. H. et al., *Neuroscience Absts. 14*, 144(1988).
Reifenrath, W.G. et al., *J. Med Chem 23*: 985–90 (1980).
Gao, Yigong et al., *J. Med Chem. 33*:39–44 (1990).
Steinman, M., et al., *J. Med. Chem. 16*(12): 1354–60 (1973).
Holladay, Mark W. et al., *Tetrahedron Letters*, 24(41): 4401–4404 (1983).
Sasaki, Yusuke, et al, *Peptides 8*: 119–121 (1987).
Barnes, Peter J., *Lancet* pp. 242–244 (Feb. 1, 1986).
Payan, Donald G., et al., Am. Rev. Respir. Dis. 136: S39–S43 (1987).
Devillier, Philippe, et al., . . . vol. 314 (20): 1323.
TenBrink, Ruth E., *J. Org. Chem. 52*: 418–422 (1987).
Buck, Stephen H., et al., *Science 226*: 987–989 (1984).
Spatola, Arno F., et al., *Tetrahedron 44*(3): 821–833 (1988).

\* cited by examiner

```
                         SEQUENCE LISTING (1) GENERAL INFORMATION:

(iii) NUMBER OF SEQUENCES: 37

(2) INFORMATION FOR SEQ ID NO:1:

(i) SEQUENCE CHARACTERISTICS:
         (A) LENGTH: 10 amino acids
         (B) TYPE: amino acid
         (D) TOPOLOGY: linear (ii) MOLECULE TYPE: peptide (xi) SEQUENCE DESCRIPTION: SEQ ID NO:1:

His Lys Thr Asp Ser Phe Val Gly Leu Xaa
1               5                   10

(2) INFORMATION FOR SEQ ID NO:2:

(i) SEQUENCE CHARACTERISTICS:
         (A) LENGTH: 7 amino acids
         (B) TYPE: amino acid
         (D) TOPOLOGY: linear (ii) MOLECULE TYPE: peptide (xi) SEQUENCE DESCRIPTION: SEQ ID NO:2:

Asp Ser Phe Val Gly Xaa Xaa
1               5

(2) INFORMATION FOR SEQ ID NO:3:

(i) SEQUENCE CHARACTERISTICS:
         (A) LENGTH: 7 amino acids
         (B) TYPE: amino acid
         (D) TOPOLOGY: linear (ii) MOLECULE TYPE: peptide (xi) SEQUENCE DESCRIPTION: SEQ ID NO:3:

Xaa Xaa Phe Val Gly Xaa Xaa
1               5

(2) INFORMATION FOR SEQ ID NO:4:

(i) SEQUENCE CHARACTERISTICS:
         (A) LENGTH: 6 amino acids
         (B) TYPE: amino acid
         (D) TOPOLOGY: linear (ii) MOLECULE TYPE: peptide (xi) SEQUENCE DESCRIPTION: SEQ ID NO:4:

Xaa Phe Val Gly Xaa Xaa
```

```
1               5
```

(2) INFORMATION FOR SEQ ID NO:5:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:5:

```
Xaa Phe Val Gly Xaa Xaa
1               5
```

(2) INFORMATION FOR SEQ ID NO:6:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:6:

```
Asp Ser Phe Val Xaa Xaa Xaa
1               5
```

(2) INFORMATION FOR SEQ ID NO:7:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:7:

```
Xaa Phe Phe Gly Xaa Xaa
1               5
```

(2) INFORMATION FOR SEQ ID NO:8:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:8:

```
Xaa Ser Phe Val Gly Xaa Xaa
1               5
```

(2) INFORMATION FOR SEQ ID NO:9:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:9:

```
Xaa Xaa Phe Val Gly Xaa Xaa
1               5
```

(2) INFORMATION FOR SEQ ID NO:10:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO:10:

Xaa Xaa Phe Val Gly Xaa Xaa
1               5

(2) INFORMATION FOR SEQ ID NO:11:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO:11:

Xaa Ser Phe Val Xaa Xaa Xaa
1               5

(2) INFORMATION FOR SEQ ID NO:12:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO:12:

Asp Ser Xaa Xaa Gly Leu Xaa
1               5

(2) INFORMATION FOR SEQ ID NO:13:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (xi) SEQUENCE DESCRIPTION: SEQ ID NO:13:

Xaa Xaa Xaa Xaa Gly Leu Xaa
1               5

(2) INFORMATION FOR SEQ ID NO:14:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (xi) SEQUENCE DESCRIPTION: SEQ ID NO:14:

Xaa Xaa Gly Leu Xaa
1               5

(2) INFORMATION FOR SEQ ID NO:15:

(i) SEQUENCE CHARACTERISTICS:
            (A) LENGTH: 6 amino acids
            (B) TYPE: amino acid (D) TOPOLOGY: linear (ii) MOLECULE TYPE: peptide (xi) SEQUENCE DESCRIPTION: SEQ ID NO:15:

Xaa Xaa Gly Leu Xaa Xaa
1               5

(2) INFORMATION FOR SEQ ID NO:16:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:16:

Xaa Xaa Xaa Gly Leu Xaa
1               5

(2) INFORMATION FOR SEQ ID NO:17:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:17:

Xaa Xaa Xaa Gly Leu Xaa
1               5

(2) INFORMATION FOR SEQ ID NO:18:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:18:

Asp Ser Xaa Xaa Gly Leu Xaa
1               5

(2) INFORMATION FOR SEQ ID NO:19:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:19:

Asp Ser Xaa Xaa Xaa Leu Xaa
1               5

(2) INFORMATION FOR SEQ ID NO:20:

(i) SEQUENCE CHARACTERISTICS:
        (A) LENGTH: 6 amino acids
        (B) TYPE: amino acid
        (D) TOPOLOGY: linear (ii) MOLECULE TYPE: peptide

```
    (xi) SEQUENCE DESCRIPTION: SEQ ID NO:20:

Xaa Xaa Xaa Gly Leu Xaa
1               5

(2) INFORMATION FOR SEQ ID NO:21:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:21:

Asp Ser Phe Val Gly Xaa Xaa
1               5

(2) INFORMATION FOR SEQ ID NO:22:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:22:

Xaa Xaa Phe Val Gly Xaa Xaa
1               5

(2) INFORMATION FOR SEQ ID NO:23:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:23:

Xaa Phe Val Xaa
1

(2) INFORMATION FOR SEQ ID NO:24:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:24:

Xaa Phe Val Gly
1

(2) INFORMATION FOR SEQ ID NO:25:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:25:

Xaa Phe Val Gly Xaa Xaa
1               5
```

(2) INFORMATION FOR SEQ ID NO:26:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:26:

Xaa Phe Val Gly Xaa Xaa
1           5

(2) INFORMATION FOR SEQ ID NO:27:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:27:

Asp Ser Phe Val Xaa Xaa Xaa
1           5

(2) INFORMATION FOR SEQ ID NO:28:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:28:

Xaa Phe Phe Gly Xaa Xaa
1           5

(2) INFORMATION FOR SEQ ID NO:29:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:29:

Asp Xaa Xaa Val Gly Leu Xaa
1           5

(2) INFORMATION FOR SEQ ID NO:30:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:30:

Xaa Xaa Xaa Val Gly Leu Xaa
1           5

(2) INFORMATION FOR SEQ ID NO:31:

```
    (i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:31:

Xaa Gly Leu Xaa
1

(2) INFORMATION FOR SEQ ID NO:32:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:32:

Val Gly Leu Xaa
1

(2) INFORMATION FOR SEQ ID NO:33:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:33:

Xaa Xaa Val Gly Leu Xaa
1               5

(2) INFORMATION FOR SEQ ID NO:34:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:34:

Xaa Xaa Val Gly Leu Xaa
1               5

(2) INFORMATION FOR SEQ ID NO:35:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:35:

Xaa Xaa Xaa Val Gly Leu Xaa
1               5

(2) INFORMATION FOR SEQ ID NO:36:

(i) SEQUENCE CHARACTERISTICS:
        (A) LENGTH: 7 amino acids
        (B) TYPE: amino acid
        (D) TOPOLOGY: linear
```

```
        (ii) MOLECULE TYPE: peptide (xi) SEQUENCE DESCRIPTION: SEQ ID NO:36:

Asp Ser Xaa Xaa Xaa Leu Xaa
1                   5

(2) INFORMATION FOR SEQ ID NO:37:

(i) SEQUENCE CHARACTERISTICS:
              (A) LENGTH: 6 amino acids
              (B) TYPE: amino acid
              (D) TOPOLOGY: linear (ii) MOLECULE TYPE: peptide (xi) SEQUENCE DESCRIPTION: SEQ ID NO:37:

Xaa Phe Xaa Xaa Leu Xaa
1               5
```

FLUORINATED NEUROKININ A ANTAGONISTS

CROSS-REFERENCE TO RELATED APPLICATION

This is a continuation, of application Ser. No. 08/282, 3471 filed Jul. 29, 1994 ; which is a continuation of application Ser. No. 08/033,987 filed Mar. 19, 1993, now abandoned; which is a continuation of application Ser. No. 07/709,092 filed May 31, 1991, now abandoned; which is a Continuation-In-Part of application Ser. No. 07/686,593 filed Apr. 17, 1991, now abandoned; which is a Continuation-In-Part of application Ser. No. 07/356,031 filed May 23, 1989, new abandoned; which is a Continuation-In-Part of application Ser. No. 07/315,202, filed Feb. 24, 1989, now abandoned which is a continuation of Application Ser. No. 07/208,926, filed Jun. 20, 1988, now abandoned; which is herein incorporated by reference.

FIELD OF THE INVENTION

This invention relates to novel peptide derivatives which are antagonists of neurokinin A.

SUMMARY OF THE INVENTION

The present invention comprises a peptide derivative of formula I:

$$X-A_1-A_2-A_3-A_4-A_5-A_6-A_7 \qquad I$$

wherein X is Y or YT.

Y is hydrogen, an alkyl of from 1–6 carbons, an acyl group of from 2–10 carbon atoms, or $B_1$ and $B_2$, wherein $B_1$ and $B_2$ are each independently selected from the group consisting of an alkyl of from 1–6 carbons or an acyl group of from 2–10 carbon atoms, with the proviso that only one of $B_1$ or $B_2$ is the acyl group. T is selected from the group consisting of 1–3 amino acid residues;

$A_1$ is -Asp-, -Glu- or a bond;
$A_2$ is -Ser-, -Thr-, -Ala-, -Asp-, -Glu-, -Val-, Tyr or PyroGlu;
$A_3$ is -Trp-, -Phe-, -β-(Napthyl)Ala-, or -Tyr-;
$A_4$ is -Val-, -Leu-, -Ile- or Phe;
$A_5$ is -Gly-, -Ala-, -Trp- or β-Ala;
$A_6$ is -Val-, -Leu-, -Ile-, -Trp- or -Phe-; and
$A_7$ is a residue of an amino acid derivative selected from the group consisting of Methioninol, Methioninamide, Norleucinol, Norleucinamide, Leucinol, Leucinamide, Argininol, Argininamide, Phenylalaninol or Phenylalaninamide.

The peptide derivative of Formula I is further characterized by modifying one of the peptide bonds between the amino acid residues of $A_1$–$A_2$, $A_2$–$A_3$, $A_3$–$A_4$, $A_4$–$A_5$, $A_5$–$A_6$, or $A_6$–$A_7$ to a modified peptide bond of $$-CH_2N-\atop\mid\atop Q$$

wherein Q is $CH_2CF_3$, $CH_2CHF_2$, $CH_2CH_2F$, or $CH_2CF_2CF_3$; or a pharmaceutically acceptable salt of Formula I.

The compounds of Formula I are useful in treating subjects in need of therapy where antagonism of neurokinin A is beneficial.

DETAILED DESCRIPTION OF THE INVENTION

Neurokinin A is a naturally occurring peptide having the formula of His-Lys-Thr-Asp-Ser-Phe-Val-Gly-Leu-Met(NH$_2$)-SEQ ID NO:1. Neurokinin A is widely distributed within body tissues and has a variety of typically undesirable biological effects.

The present invention comprises a new class of neurokinin A antagonists useful for treating maladies associated with the release of neurokinin A in a subject. For example, the compounds of the present invention are useful as immunosuppressants, and for treating subjects with various conditions such as arthritis, asthma, urinary incontinence, pain, inflammation, gastrointestinal hypermotility, neuritis, neuralgia, and headache, including migrane. "Subject" as used herein means mammals such as humans, sheep, horses, cattle, pigs, dogs, cats, rats and mice.

The compounds of the present invention are peptide derivatives of formula I:

$$X-A_1-A_2-A_3-A_4-A_5-A_6-A_7 \qquad I$$

wherein:

X is

Y, wherein Y is hydrogen, an alkyl of from 1–6 carbons, an acyl group of from 2–10 carbon atoms, or $B_1$ and $B_2$, wherein $B_1$ and $B_2$ are each independently selected from the group consisting of an alkyl of from 1–6 carbons or an acyl group of from 2–10 carbon atoms, with the proviso that $B_1$ or $B_2$ are not simultaneously the acyl group, or YT, wherein T is from 1 to 3 amino acid residues;

$A_1$ is -Asp-, -Glu- or a bond;
$A_2$ is -Ser-, -Thr-, -Ala-, -Asp-, -Glu-, -Val-, Tyr or PyroGlu;
$A_3$ is -Trp-, -Phe-, -β-(Napthyl)Ala-, or -Tyr-;
$A_4$ is -Val-, -Leu-, -Ile-, or Phe;
$A_5$ is -Gly-, -Ala-, -Trp- or β-Ala;
$A_6$ is -Val-, -Leu-, -Ile-, -Trp- or -Phe-; and
$A_7$ is a residue of an amino acid derivative selected from the group consisting of Methioninol, Methioninamide, Norleucinol, Norleucinamide, Leucinol, Leucinamide, Argininol, Argininamide, Phenylalaninol or Phenylalaninamide.

The peptide derivative of Formula I is further characterized by modifying at least one peptide bond (—CONH—) between the residues of $A_1$–$A_2$, when $A_1$ is not a bond, $A_2$–$A_3$, $A_3$–$A_4$, $A_4$–$A_5$, $A_5$–$A_6$, or $A_6$–$A_7$ to a modified peptide bond having the formula:

$$-CH_2N-\atop\mid\atop Q$$

wherein Q is $CH_2CF_3$, $CH_2CHF_2$, $CH_2CH_2F$, or $CH_2CF_2CF_3$, or a pharmaceutically acceptable salt of Formula I.

The abbreviations and nomenclature used herein are described as follows:

| Abbreviations | Compounds |
| --- | --- |
| 1) Ala | Alanine |
| 2) Asp | Aspartic Acid |
| 3) Glu | Glutamic acid |
| 4) Ile | Isoleucine |
| 5) Leu | Leucine |
| 6) Phe | Phenylalanine |
| 7) Ser | Serine |
| 8) Thr | Threonine |
| 9) Trp | Tryptophan |
| 10) Tyr | Tyrosine |
| 11) Val | Valine |
| 12) β-(Napthyl)Ala | β-(Napthyl) Alanine |
| 13) β-Ala | β-Alanine |
| 14) PyroGlu | PyroGlutamic Acid |
| The following are amide derivatives of amino acids where the hydroxyl group (—OH) of the terminal carboxyl group (—COOH) has been replaced by an amino group (—$NH_2$): | |
| 15) Met($NH_2$) | Methioninamide |
| 16) Nle($NH_2$) | Norleucinamide |
| 17) Leu($NH_2$) | Leucinamide |
| 18) Arg($NH_2$) | Argininamide |
| 19) Phe($NH_2$) | Phenylalaninamide |
| The following are alcohol derivatives of amino acids where the terminal carboxyl group (—COOH) is replaced by (—$CH_2OH$). | |
| 20) Met($CH_2OH$) | Methioninol |
| 21) Nle($CH_2OH$) | Norleucinol |
| 22) Leu($CH_2OH$) | Leucinol |
| 23) Arg($CH_2OH$) | Argininol |
| 24) Phe($CH_2OH$) | Phenylalaninol |

The term "amino acid" as used herein includes the naturally occurring amino acids as well as other "non-protein" α-amino acids commonly utilized by those in the peptide chemistry arts when preparing synthetic analogs of naturally occurring peptides. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, arginine, ornithine, and lysine.

Examples of "non-protein" α-amino acids are norleucine, norvaline, alloisoleucine, homoarginine, thiaproline, dehydroproline, hydroxyproline, homoserine, cyclohexylglycine, α-amino-n-butyric acid, cyclohexylalanine, homophenylalanine, phenylalanines substituted at the ortho, meta, or para position of the phenyl moiety with one or two of the following, a ($C_1$–$C_4$) alkyl, ($C_1$–$C_4$) alkoxy, halogen, or nitro groups or substituted with a methylenedioxy group, β-2- and 3-thienylalanine, β-2- and 3-furanylalanine, β-2-, 3-, and 4-pyridylalanine, β-(benzothienyl-2- and 3-yl)alanine, 62 -(1- and 2-naphthyl) alanine, O-alkylated derivates of serine, threonine, or tyrosine, S-alkylated cysteine, the O-sulfate ester of tyrosine, 3,5-diiodo-tyrosine and the D-isomers of the naturally occurring amino acids.

The natural amino acids with the exception of glycine, contain a chiral carbon atom. Unless otherwise specifically indicated, the optically active amino acids used in accordance with the present invention may be either the D or the L configuration, the L configuration being preferred. As is customary, the structure of peptides written out herein is such that the amino terminal end is on the left side of the chain and the carboxy terminal end is on the right side of the chain.

When two or more amino acids combine to form a peptide, the elements of water are removed, and what remains of each amino acid is called a residue. "Residue" is therefore an amino acid that lacks a hydrogen atom of the terminal amino group, and/or lacks the hydroxyl group of the terminal carboxyl group. Using accepted terminology, a dash (-)in front of (indicating loss of a hydrogen) and/or after (indicating loss of the hydroxyl) a three letter code for an amino acid or amino acid derivative indicates a residue.

Referring to Formula I, the moiety "X" may be any atom or group of atoms that do not adversely effect the function of the compound as described herein. X can be Y, wherein Y is hydrogen, an alkyl of from 1–6 carbons or an acyl group of from 2–10 carbon atoms. An "alkyl of from 1–6 carbons" means straight, branched or cyclic alkyls such as methyl, ethyl, propyl, isopropyl, butyl, isobutyl, tert-butyl, pentyl, isopentyl, sec-pentyl, cyclopentyl, hexyl, cyclohexyl, and isohexyl. An "acyl group of from 2 to 10 carbon atoms" means straight, branched, cyclic, saturated and unsaturated acyl groups having 1 or 2 carbonyl moieties per group, for example, acetyl, benzoyl, succinyl, maleyl, and glutaryl. Preferably, Y is hydrogen.

Alternatively, Y can be $B_1$ and $B_2$. Each of $B_1$ and $B_2$ in connected to the alpha amino of the amino terminal amino acid thereby replacing hydrogen atoms normally attached to the nitrogen atom of an amino acid. $B_1$ and $B_2$ are independently selected from a group consisting of an alkyl of from 1–6 carbons or an acyl group of from 2–10 carbon atoms as previously defined. It is preferred that $B_1$ and $B_2$ are not simultaneously the acyl group.

X can also be YT, wherein Y is as previously defined and T is a group of from 1 to 3 amino acid residues. T is connected to $A_1$, or when $A_1$ is a bond T can be connected to $A_2$. These amino acid residues are selected from residues which do not adversely effect the activity of the compound. Preferred amino acid residues for T are Thr-, Lys-Thr- and His-Lys-Thr-.

In accordance with the present invention, the amino terminal amino acid can be an amino acid as defined by T, $A_1$ or $A_2$. As previously described, T may or may not be present in the compounds of the present invention. $A_1$ is also optionally present in the compounds of the present invention since $A_1$ may be a bond. When T is not present and when $A_1$ is a bond, $A_2$ is the amino terminal amino acid to which Y is attached.

Formula I of the present invention is further characterized by at least one modified peptide bond between any of the amino acid residues described herein.

Preferably, the modified peptide bond is between one of $A_1$–$A_2$, when $A_1$ is not a bond, $A_2$–$A_3$, $A_3$–$A_4$, $A_4$–$A_5$, $A_5$–$A_6$, or $A_6$–$A_7$, wherein the typical peptide bond of —CONH— between two amino acids is replaced with a reduced amide of the formula

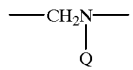

Using conventional methods of identification, this is characterized as

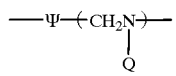

with the symbol "Ψ" designating a modified peptide bond. An example follows using the terminology as defined herein when X is hydrogen, $A_1$ is -Ala-, $A_2$ is -Ser-, $A_3$ is -Phe-, $A_4$ is -Val-, $A_5$ is -Gly-, $A_6$ is -Leu- and $A_7$ is Leucinamide, and the modified peptide bond is between $A_6$ and $A_7$ with Q as $CH_2CF_3$:

Asp-Ser-Phe-Val-Gly-LeuΨ($CH_2NCH_2CF_3$)Leu($NH_2$)—SEQ ID NO:2.

The modified peptide bond of the present invention is a reduced amide (—CH$_2$N—) with a fluorinated alkyl (Q) attached via the alkyl to the nitrogen atom of the reduced amide. Examples of some modified peptide bonds used in accordance with the present invention follow:

a) CH$_2$NCH$_2$CF$_3$,
b) CH$_2$NCH$_2$CHF$_2$,
c) CH$_2$NCH$_2$CH$_2$F, and
d) CH$_2$NCH$_2$CF$_2$CF$_3$.

Of the foregoing modified peptide bonds, CH$_2$NCH$_2$CF$_3$ designated as (a) above, where Q is —CH$_2$CF$_3$, is preferred.

The compound of the present invention comprises at least one modified peptide bond as defined herein. Preferably, only one of the modified peptide bonds is present in the compound of the present invention, and, more preferably, the modified peptide bond is between A$_6$ and A$_7$.

The peptide derivatives of formula I can form pharmaceutically acceptable salts with any non-toxic, organic or inorganic acid. Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid.

The compounds of Formula I wherein A$_7$ is an amino acid residue as previously described wherein the —COOH group is replaced with a —CONH$_2$ group, the reduced amide bond substitution represented by —-Ψ[CH$_2$-N(Q)] is located between amino acid residues of A$_6$–A$_7$ and X is hydrogen can be prepared by techniques and procedures well known and appreciated by one of ordinary skill in the art. General synthetic procedures for preparing these compounds is set forth in Scheme A. In Scheme A, all substituents unless otherwise indicated are as previously defined.

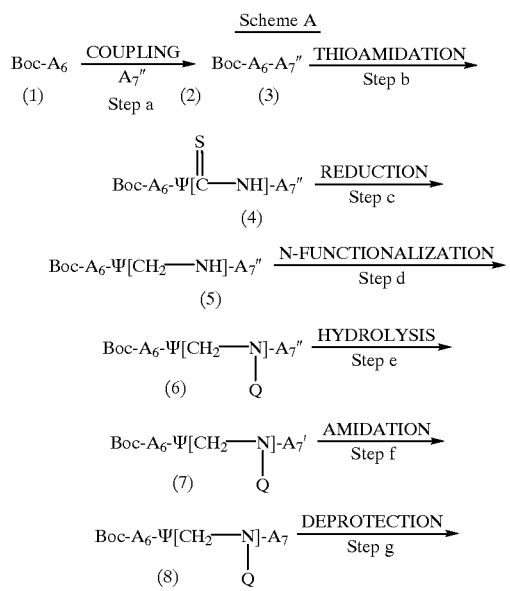

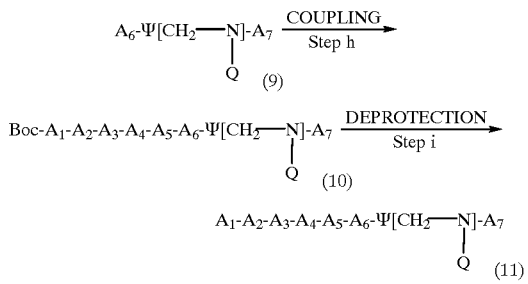

A$_7''$ = A$_7$ as previously defined wherein the —COOH group is replaced with —C(O)OCH$_3$
A$_7'$ = A$_7$ as previously defined wherein the —COOH group is not replaced Scheme A

STEP A:

The appropriate Boc-A$_6$ amino acid of structure (1) is coupled with the appropriate A$_7$ amino acid methyl ester of structure (2) to give the corresponding Boc-A$_6$–A$_7$ peptide methyl ester of structure (3).

For example, the appropriate Boc-A$_6$ amino acid of structure (1) is contacted with an equimolar amount of an appropriate A$_7$ amino acid methyl ester hydrochloride salt of structure (2), an equimolar amount of a coupling agent such as a mixture of 1-(3-dimethylaminopropyl)-3-ethylcarbodiimide hydrochloride (EDC) and 1-hydroxybenzotriazole hydrate and a equimolar amount of a suitable non-nucleophilic amine such as diisopropylethylamine. The reactants are typically contacted in a suitable aprotic organic solvent such as methylene chloride or tetrahydrofuran. The reactants are typically stirred together at room temperature under a nitrogen atmosphere for 2–24 hours. The Boc-A$_6$–A$_7$ peptide methyl ester of structure (3) is recovered from the reaction zone by extractive methods known in the art. It may be purified by chromatography.

The selection of an appropriate coupling reagent is within the skill of the art. A particularly suitable coupling reagent where the amino acid to be added is Asp is N,N'-diisopropylcarbodiimide and 1-hydroxy-benzotriazole. The use of these reagents prevents nitrile and lactam formation. Other coupling agents are (1) carbodiimides (e.g., N,N-dicyclohexylcarbodiimide; (2) cyanamides (e.g., N,N-dibenzylcyanamide); (3) ketenimines; (4) isoxazolium salts (e.g., N-ethyl-5-phenyl-isoxazolium-3'-sulfonate; (5) monocyclic nitrogen containing heterocyclic amides of aromatic character containing one through four nitrogens in the ring such as imidazolides, pyrazolides, and 1,2,4-triazolides. Specific heterocyclic amides that are useful include N,N'-carbonyldiimidazole and N,N-carbonyl-di-1,2,4-triazole; (6) alkoxylated acetylene (e.g., ethoxyacetylene); (7) reagents which form a mixed anhydride with the carboxyl moiety of the amino acid (e.g., ethylchloroformate and isobutylchloroformate) or the symmetrical anhydride of the amino acid to be coupled (e.g., Boc-Phe-O-Phe-Boc) and (8) nitrogen containing heterocyclic compounds having a hydroxy group on one ring nitrogen (e.g., N-hydroxyphthalimide, N-hydroxysuccinimide and 1-hydroxy-benzotriazole). Other activating reagents and their use in peptide coupling are described by Kapoor, *J. Pharm. Sci.*, 59 1–27 1970, which is incorporated herein by reference.

STEP B:

The amide functionality of the appropriate Boc-A$_6$–A$_7$ peptide methyl ester of structure (3) is thioamidated to give the corresponding Boc-$A_6$-Ψ[C(S)-NH]-$A_7$ peptide methyl ester of structure (4).

For example, the appropriate Boc-$A_6$–$A_7$ peptide methyl ester of structure (3) is contacted with a equimolar amount of an appropriate thioamidating reagent such as 2,4-bis (phenylthio)-1,3-dithio-2.4-diphosphetane-2,4-dithione. The reactants are typically contacted in a suitable aprotic organic solvent such as anhydrous tetrahydrofuran. The reactants are typically stirred together at room temperature under a nitrogen atmosphere for a period of time ranging from 2–24 hours. The Boc-$A_6$-Ψ[C(S)-NH]-$A_7$ peptide methyl ester of structure (4) is recovered from the reaction zone by extractive methods as is known in the art. It may be purified by chromatography.

STEP C:

The thioamide functionality of the appropriate Boc-A6-Ψ[C(S)-NH]-$A_7$ peptide methyl ester of structure (4) is reduced to give the corresponding Boc-$A_6$-Ψ[$CH_2$-NH]-$A_7$ peptide methyl ester of structure (5).

For example, the appropriate Boc-$A_6$-Ψ[C(S)-NH]-$A_7$ peptide methyl ester of structure (4) is contacted with a molar excess of a suitable reducing agent such as a mixture of nickel chloride hexahydrate ($NiCl_2 \cdot 6H_2O$) and sodium borohydride. The reactants are typically contacted in a suitable organic solvent such as a mixture of tetrahydrofuran and methanol. The reactants are typically stirred together for a period of time ranging from 5 minutes to 5 hours and at a temperature range of from –10° C. to room temperature. The Boc-$A_6$-Ψ[$CH_2$-NH]-$A_7$ peptide methyl ester of structure (5) is recovered from the reaction zone by filtration and evaporation of the solvent. It may be purified by chromatography.

STEP D:

The amino functionality of the appropriate Boc-$A_6$-Ψ[$CH_2$-NH]-$A_7$ peptide methyl ester of structure (5) is functionalizde to give the corrsponding Boc-$A_6$-Ψ[$CH_2$-N(Q)]-$A_7$ peptide methyl ester of structure (6).

For example, when the desired amino functionality is 2,2,2-trifluoroethyl, the appropriate Boc-$A_6$-Ψ[$CH_2$-NH]-$A_7$ peptide methyl ester of structure (5) is contacted with a molar excess of an appropriate alkylating agent such as 2,2,2-trifluoroethyl trifluoromethanesulfonate and an appropriate non-nucleophilic base such as triethylamine. The reactants are typically contacted in a suitable aprotic organic solvent such as benzene. The reactants are typically stirred together for a period of time ranging from 5 hours to 10 days at a temperature range of from room temperature to ref lux. The Boc-$A_6$-Ψ[$CH_2$-N($CH_2CF_3$)]-$A_7$ peptide methyl ester of structure (6) is recovered from the reaction zone by extractive methods as is known in the art. It may be purified by chromatography.

Alternatively, when the desired amino functionality is 2,2-difluoroethyl, the appropriate Boc-$A_6$-Ψ[$CH_2$-NH]-$A_7$ peptide methyl ester of structure (5) is contacted with a molar excess of an appropriate alkylating agent such as 2,2-difluoroethyl trifluoromethanesulfonate and an appropriate non-nucleophilic base such as triethylamine. The reactants are typically contacted in a suitable aprotic organic solvent such as benzene. The reactants are typically stirred together for a period of time ranging from 5 hours to 10 days at a temperature range of from room temperature to reflux. The Boc-$A_6$-Ψ[$CH_2$-N($CH_2CHF_2$)]-$A_7$ peptide methyl ester of structure (6) is recovered from the reaction zone by extractive methods known in the art. It may be purified by chromatography.

Alternatively, when the desired amino functionality is 2-fluoroethyl, the appropriate Boc-$A_6$-Ψ[$CH_2$-NH]-$A_7$ peptide methyl ester of structure (5) is contacted with a molar excess of an appropriate alkylating agent such as 2-fluoroethyl p-toluenesulfonate and an appropriate non-nucleophilic base such as triethylamine. The reactants are typically contacted in a suitable aprotic organic solvent such as benzene. The reactants are typically stirred together for a period of time ranging from 5 hours to 10 days at a temperature range of from room temperature to reflux. The Boc-$A_6$-Ψ[$CH_2$-N($CH_2CH_2F$)]-$A_7$ peptide methyl ester of structure (6) is recovered from the reaction zone by extractive methods as is known in the art. It may be purified by chromatography.

Alternatively, when the desired amino functionality is 3,3,3-trifluoro-2,2-difluoropropyl, the appropriate Boc-$A_6$-Ψ[($CH_2$-NH]-$A_7$ peptide methyl ester of structure (5) is contacted with a molar excess of an appropriate alkylating agent such as 3,3,3-trifluoro-2,2-difluorpropyl trichloromethanesulfonate and an appropriate non-nucleophilic base such as triethylamine. The reactants are typically contacted in a suitable aprotic organic solvent such as benzene. The reactants are typically stirred together for a period of time ranging from 5 hours to 10 days at a temperature range of from room temperature to reflux, The Boc-$A_6$-Ψ[$CH_2$-N($CH_2CF_2CF_3$)]-$A_7$ peptide methyl ester of structure (6) is recovered from the reaction zone by extractive methods as is known in the art. It may be purified by chromatography.

STEP E:

The methyl ester functionality of the appropriate Boc-$A_6$-Ψ[$CH_2$-N(Q)]-$A_7$ peptide methyl ester of structure (6) is hydrolyzed to give the corresponding Boc-$A_6$-Ψ[$CH_2$-N(Q)]-$A_7$ peptide of structure (7).

For example, the appropriate Boc-$A_6$-Ψ[$CH_2$-N(Q)]-$A_7$ peptide methyl ester of structure (6) is contacted with a molar excess of an appropriate base such as aqueous sodium hydroxide. The reactants are typically contacted in a suitable protic solvent such as ethanol. The reactants are typically stirred together at room temperature for a period of time ranging from 2–24 hours. The Boc-$A_6$-Ψ[$CH_2$-N(Q)]-$A_7$ peptide of structure (7) is recovered from the reaction zone by acidification followed by extractive methods as is known in the art. It may be purified by chromatography.

STEP F:

The carboxylic acid functionality of the appropriate Boc-$A_6$-Ψ[$CH_2$-N(Q)]-$A_7$ peptide of structure (7) is amidated to give the corresponding Boc-$A_6$-Ψ[$CH_2$-N(Q)]-$A_7$ peptide amide of structure (8).

For example, the appropriate Boc-$A_6$-Ψ[$CH_2$-N(Q)]-$A_7$ peptide of structure (7) is contacted with an equimolar amount of an activating agent such as isobutylchloroformate, an equimolar amount of an appropriate non-nucleophilic amine such as triethylamine and an excess amount of ammonia. The reactants are typically contacted in a suitable organic solvent such as ethyl acetate. The reactants are typically stirred together for a period of time ranging from 2–24 hours and at a temperature range of from –20° C. to room temperature. The Boc-$A_6$-Ψ[$CH_2$-N(Q)]-$A_7$ peptide amide of structure (8) is recovered from the reaction zone by extractive methods as is known in the art. It may be purified by chromatography.

STEP G:

The Boc protecting group of the appropriate Boc-$A_6$-Ψ[$CH_2$-N(Q)]-$A_7$ peptide amide of structure (8) is hydrolyzed to give the corresponding $A_6$-Ψ[$CH_2$-N(Q)]-$A_7$ peptide amide of structure (9).

For example, the appropriate Boc-$A_6$-Ψ[$CH_2$-N(Q)]-$A_7$ peptide amide of structure (8) is contacted with a suitable acid, such as anhydrous hydrochloric acid or trifluoroacetic acid. The reactants are typically contacted in a suitable polar organic solvent such as dioxane. The reactants are typically stirred together at room temperature for a period of time ranging from 2–24 hours. The $A_6$-Ψ[$CH_2$-N(Q)]-$A_7$ peptide amide of structure (9) is recovered from the reaction zone by evaporation of the solvents. It may be purified by chromatography.

STEP H:

The appropriate $A_6$-Ψ[$CH_2$-N(Q)]-$A_7$ peptide amide of structure (9) is coupled to give the corresponding Boc-$A_1$-$A_2$-$A_3$-$A_4$-$A_5$-$A_6$-Ψ[$CH_2$-N(Q)]-$A_7$ peptide amide of structure (10).

For example, the appropriate $A_6$-Ψ[$CH_2$-N(Q)]-$A_7$ peptide amide of structure (9) can be coupled via a sequential condensation with the appropriate Boc-$A_5$ amino acid as described previously in step a, followed by removal of the Boc protecting group on the $A_5$ amino acid as described previously in step g. The resulting $A_5$-$A_6$-Ψ[$CH_2$-N(Q)]-$A_7$ peptide amide may then be coupled with the appropriate Boc-$A_4$ amino acid, followed by removal of Boc protecting group on the $A_4$ amino acid. This procedure is repeated with the appropriate Boc-$A_3$ amino acid, the appropriate BoC-$A_2$ amino acid and ending with the appropriate Boc-$A_1$ amino acid to give the Boc-$A_1$-$A_2$-$A_3$-$A_4$-$A_5$-$A_6$-Ψ[$CH_2$-N(Q)]-$A_7$ peptide amide of structure (10).

Alternatively, the appropriate $A_6$-Ψ[$CH_2$-N(Q)]-$A_7$ peptide amide of structure (9) can be coupled via a fragment condensation with the appropriate preformed Boc-$A_1$-$A_2$-$A_3$-$A_4$-$A_5$ peptide to give the Boc-$A_1$-$A_2$-$A_3$-$A_4$-$A_5$-$A_6$-Ψ[$CH_2$-N(Q)]-$A_7$ peptide amide of structure (10) as described previously in step a.

In addition, any combination of sequential and fragment condensations may be utilized for the coupling reaction in step h. For example, the appropriate $A_6$-Ψ[$CH_2$-N(Q)]-$A_7$ peptide amide of structure (9) can be coupled via a fragment condensation with the appropriate preformed Boc-$A_2$-$A_3$-$A_4$-$A_5$ peptide to give the Boc-$A_2$-$A_3$-$A_4$-$A_5$-$A_6$-Ψ[$CH_2$-N(Q)]-$A_7$ peptide amide as described previously in step a. The Boc protecting group on the $A_2$ amino acid is then removed to give the $A_2$-$A_3$-$A_4$-$A_5$-$A_6$-Ψ[$CH_2$-N(Q)]-$A_7$ peptide amide as described previously in step g. The $A_2$-$A_3$-$A_4$-$A_5$-$A_6$-Ψ[$CH_2$-N(Q)]-$A_7$ peptide amide is then coupled with appropriate Boc-$A_1$ amino acid to give the Boc-$A_1$-$A_2$-$A_3$-$A_4$-$A_5$-$A_6$-Ψ[$CH_2$-N(Q)]-$A_7$ peptide amide of structure (10) as described previously in step a.

The α-amino protecting group employed with each amino acid introduced into the polypeptide sequence may be any such protecting group known to the art. Among the classes of α-amino protecting groups contemplated are (1) acyl type protecting groups such as: formyl, trifluoroacetyl, phthalyl, toluenesulfonyl (tosyl), benzenesulfonyl, nitrophenylsulfenyl, tritylsulfenyl, o-nitrophenoxyacetyl and α-chlorobutyryl; (2) aromatic urethane type protecting groups such as benzyloxycarbonyl and substituted benzyloxycarbonyl, such as p-chlorobenzyloxycarbonyl, p-nitrobenzyloxycarbonyl, p-bromobenzyloxycarbonyl, p-methoxybenzyloxycarbonyl, 1-(p-biphenylyl)-1-methylethoxy-carbonyl, α, α-dimethyl-3,5-dimethoxybenzyloxycarbonyl and benzhydryloxycarbonyl; (3) aliphatic urethane protecting groups such as tert-butyloxycarbonyl (Boc), diisopropyl-methoxycarbonyl, isopropyloxycarbonyl, ethoxycarbonyl and allyloxycarbonyl; (4) cycloalkyl urethane type protecting groups such as cyclopentyloxycarbonyl, adamantyloxycarbonyl and cyclohexyloxycarbonyl; (5) thio urethan type protecting groups such as phenylthiocarbonyl; (6) alkyl type protecting groups such as triphenylmethyl (trityl) and benzyl; and (7) trialkylsilane groups such as trimethylsilane. The preferred α-amino protecting group is tert-butyloxycarbonyl (Boc).

STEP I:

The Boc protecting group on $A_1$ and various other protecting groups on amino acids $A_1$–$A_7$ of the appropriate Boc-$A_1$-$A_2$-$A_3$-$A_4$-$A_5$-$A_6$-Ψ[$CH_2$-N(Q) ]-$A_7$ peptide amide of structure (10) are removed by methods well known in the art to give the corresponding $A_1$-$A_2$-$A_3$-$A_4$-$A_5$-$A_6$-Ψ[$CH_2$-N(Q)]-$A_7$ peptide amide of structure (11).

For example, the appropriate Boc-$A_1$-$A_2$-$A_3$-$A_4$-$A_5$-$A_6$-Ψ[$CH_2$-N(Q)]-$A_7$ peptide amide of structure (10) may be subjected to a global deprotection using HF to give the corresponding fully deprotected $A_1$-$A_2$-$A_3$-$A_4$-$A_5$-$A_6$-Ψ[$CH_2$-N(Q)]-$A_7$ peptide amide of structure (11). Typically, the appropriate Boc-$A_1$-$A_2$-$A_3$-$A_4$-$A_5$-$A_6$-Ψ[$CH_2$-N(Q)]-$A_7$ peptide amide of structure (10) is dissolved in HF along with a suitable scavenger such as anisole. The reactants are typically stirred together at 0° C. for a period of time ranging from 20 minutes to 1 hour. The fully deprotected $A_1$-$A_2$-$A_3$-$A_4$-$A_5$-$A_6$-Ψ[$CH_2$-N(Q)]-$A_7$ peptide amide of structure (11) is recovered from the reaction zone by evaporation of the solvent. It may be purified by chromatography.

Starting materials for use in Scheme A are readily available to one of ordinary skill in the art. For example, 2,2,2-trifluoroethyl trifluoromethanesulfonate is described in *J.Am. Chem. Soc.* 77 6214 1955, 2,2-difluoroethyl trifluoromethanesulfonate and 2-fluoroethyl p-toluenesulfonate are described in *J.Med.Chem.* 23 985 1980 and 3,3,3-trifluoro-2,2-difluoropropyl trichloromethanesulfonate is described in *J.Med.Chem.* 16 1354 1973.

The following examples present typical syntheses as described in Scheme A. These examples are understood to be illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "mp" refers to melting point; "° C." refers to degrees Celsius; "mm Hg" refers to millimeters of mercury; "μL" refers to microliters; "μg" refers to micrograms; and "μM" refers to micromolar. The term "Boc" means t-butyloxycarbonyl, the term "β-Chxl" means β-cyclohexyl, the term "Bn" means benzyl, "OBn" means benzyloxy, and the term "Ac" means acetyl. The peptides prepared in the following examples are comprised of L-amino acid residues unless otherwise indicated.

EXAMPLE 1

Asp-Ser-Phe-Val-Gly-Leu-Ψ[$CH_2$-N($CH_2CF_3$)]-Leu (NH2) SEQ ID NO:2—MDL 102,409.

Step a: Boc-Leu-Leu(OMe)

Mix Boc-Leu hydrate (5.0 g, 20 mmol), Leu(OMe) hydrochloride (3.63 g, 20 mmol), 1-(3-dimethylaminopropyl)-3-ethylcarbodiimide hydrochloride (EDC) (3.83 g, 20 mmol), 1-hydroxybenzotriazole hydrate (3.06 g, 20 mmol), diisopropylethylamine (3.5 mL, 20 mmol) and methylene chloride (40 mL). Stir at room temperature under a nitrogen atmosphere until the reaction is complete. Dilute with ethyl acetate (25 mL), wash with cold 0.5 N hydrochloride acid, saturated aqueous sodium hydrogen carbonate and brine. Dry ($MgSO_4$) and evaporate the solvent invacuo to give the title compound (5.83 g).

Step b: Boc-Leu-Ψ[C(S)-NH]Leu(OMe)

Mix Boc-Leu-Leu(OMe) (0.36 g, 1 mmol), 2,4-bis (phenylthio)-1,3-dithio-2.4-diphosphetane-2,4-dithione (0.45 g, 1.1 mmol) and anhydrous tetrahydrofuran (3 mL). Stir at room temperature under a nitrogen atmosphere for 8 hours. Dilute with ethyl acetate and wash with 1 N hydrochloric acid, saturated sodium hydrogen carbonate and brine. Dry (MgSO$_4$) and evaporate the solvent invacuo to give the title compound.

Step c: Boc-Leu-Ψ[CH$_2$-NH]Leu(OMe)

Dissolve Boc-Leu-Ψ[C(S)-NH]Leu(OMe) (1 mmol) in a mixture of 1:1 tetrahydrofuran/methanol (10 mL). Add nickel chloride hexahydrate (NiCl$_2$•6H$_2$O) (1.9 g, 8 mmol) and cool in an ice bath. Add sodium borohydride (0.91 g, 24 mmol) and stir at room temperature under a nitrogen atmosphere for 20 minutes. Filter and evaporate the solvent invacuo to give the title compound (0.14 g, 40.6%).

Step d: Boc-Leu-Ψ[CH$_2$-N(CH$_2$CF$_3$)]Leu(OMe)

Mix Boc-Leu-Ψ[CH$_2$-NH]Leu(OMe) (0.15 g, 0.435 mmol), 2,2,2-trifluoroethyl trifluoromethanesulfonate (0.41 g, 1.74 mmol), trifluoroacetic acid (0.06 mL, 0.435 mmol) and benzene (2 mL). Heat at reflux for 7 days, occasionally adding additional 2,2,2-trifluoroethyl trifluoromethanesulfonate and trifluoroacetic acid. Cool to room temperature, wash with 1 N hydrochloric acid then saturated sodium hydrogen carbonate and brine. Dry (MgSO$_4$) and evaporate the solvent invacuo to give the title compound.

Step e: Boc-Leu-Ψ[CH$_2$-N(CH$_2$CF$_3$)]Leu

Dissolve Boc-Leu-Ψ[CH$_2$-N(CH$_2$CF$_3$)]Leu(OMe) (0.45 g, 1.055 mmol) in ethanol (10 mL) and add 1 N sodium hydroxide (10 mL). Stir at room temperature overnight. Dilute with water and acidify with 1 N hydrochloric acid. Extract into ethyl acetate, dry (MgSO$_4$) and evaporate the solvent invacuo to give the title compound (0.40 g, 92%).

Step f: Boc-Leu-Ψ[CH$_2$-N(CH$_2$CF$_3$)]Leu(NH2)

Dissolve Boc-Leu-Ψ[CH$_2$-N(CH$_2$CF$_3$)]Leu (0.40 g, 0.97 mmol) in ethyl acetate (10 mL) and cool to −20° C. Add triethylamine (0.15 mL, 1 mmol) and isobutylchloroformate (0.13 mL, 1 mmol). Stir at −20° C. for 20 minutes. Bubble ammonia gas into the reaction mixture at −20° C. for 10 minutes then allow to warm to room temperature overnight. Wash with brine and dry (MgSO$_4$). Evaporate the solvent invacuo to give the title compound (0.88 g).

Step q: Leu-Ψ[CH$_2$-N(CH$_2$CF$_3$)]Leu(NH2)•hydrochloride

Mix Boc-Leu-Ψ[CH$_2$-N(CH$_2$CF$_3$)]Leu(NH2) (0.88 g) and 4 N hydrochloric acid in dioxane (10 mL). Stir under nitrogen atmosphere until the reaction is complete. Evaporate the solvent invacuoto give the title compound (0.49 g). 298E-168

Step h: Boc-Asp(OBn)-Ser(OBn)-Phe-Val-Gly-Leu-Ψ[CH$_2$-N(CH$_2$CF$_3$)]-Leu(NH2) SEQ ID NO;3

Mix Leu-Ψ[CH$_2$-N(CH$_2$CF$_3$)]Leu(NH2)•hydrochloride (0.49 g, 1.57 mmol), Boc-Ser(OBn)-Phe-Val-Gly (0.94 g, 1.57 mmol), 1-(3-dimethylaminopropyl)-3-ethylcarbodiimide hydrochloride (EDC) (0.34 g, 1.73 mmol), 1-hydroxybenzotriazole hydrate (0.26 g, 1.73 mmol), diisopropylethylamine (0.3 g, 1.73 mmol) and methylene chloride (30 mL). Stir at room temperature under a nitrogen atmosphere until the reaction is complete. Evaporate the solvent in vacuo to give Boc-Ser(OBn)-Phe-Val-Gly-Leu-Ψ[CH$_2$-N(CH$_2$CF$_3$)]Leu(NH2) (0.84 g, 60%).

Mix Boc-Ser(OBn)-Phe-Val-Gly-Leu-Ψ[CH$_2$-N(CH$_2$CF$_3$)]Leu(NH2) SEQ ID NO:4, (0.84 g, 0.943 mmol) and 4 N hydrochloric acid in dioxane. Stir at room temperature until the reaction is complete. Evaporate the solvent in vacuo to give Ser(OBn)-Phe-Val-Gly-Leu-Ψ[CH$_2$-N(CH$_2$CF$_3$)]Leu(NH2)•hydrochloride, SEQ ID NO:5, (0.92 g). Mix Ser(OBn)-Phe-Val-Gly-Leu-Ψ[CH$_2$-N(CH$_2$CF$_3$)]Leu(NH2)•hydrochloride, SEQ ID NO:5, (829 mg, 1.0 mmol), Boc-Asp(OBn) (323 mg, 1.0 mmol), 1-(3-dimethylaminopropyl)-3-ethylcarbodiimide hydrochloride (EDC) (0.22 g, 1.1 mmol), 1-hydroxybenzotriazole hydrate (0.17 g, 1.1 mmol), diisopropylethylamine (0.29 g, 1.1. mmol) and methylene chloride (10 mL). Stir at room temperature under a nitrogen atmosphere until the reaction is complete. Evaporate the solvent invacuo to give Boc-Asp(OBn)-Ser(OBn)-Phe-Val-Gly-Leu-Ψ[CH$_2$-N(CH$_2$CF$_3$)]-Leu (NH2), SEO ID NO: 3.

Step i: Asp-Ser-Phe-Val-Gly-Leu-Ψ[CH$_2$-N(CH$_2$CF$_3$)]-Leu (NH2) SEQ ID NO:2.

Dissolve Boc-Asp(OBn)-Ser(OBn)-Phe-Val-Gly-Leu-Ψ[CH$_2$-N(CH$_2$CF$_3$)]-Leu(NH2), SEQ ID NO:3, (111 mg, 0.1 mmol) in hydrogen fluoride and anisole. Stir for 1 hour at 0° C. Allow the solvent to evaporate to give the title compound.

The following compounds can be prepared in a similar fashion to that described above in Example 1:

Asp-Ser-Phe-Val-β-Ala-Leu-Ψ[CH$_2$-N(CH$_2$CF$_3$) ]-Phe (NH$_2$) SEQ ID NO:6; and pyroGlu-Phe-Phe-Gly-Leu-Ψ[CH$_2$-N(CH$_2$CF$_3$) ]-Nle (NH$_2$) SEQ ID NO:7.

The compounds of Formula I wherein A$_7$ is an amino acid residue as previously described wherein the —COOH group is replaced with a —CONH$_2$ group, the reduced amide bond substitution represented by —Ψ[CH$_2$-N(Q)] is located between amino acid residues of A$_6$–A$_7$ and X is C$_1$–C$_6$ alkyl, C$_2$–C$_{10}$ acyl or 3 amino acid residues can be prepared by techniques and procedures well known and appreciated by one of ordinary skill in the art. General synthetic procedures for preparing these compounds are set forth in Scheme B. In Scheme B, all substituents unless otherwise indicated are as previously defined.

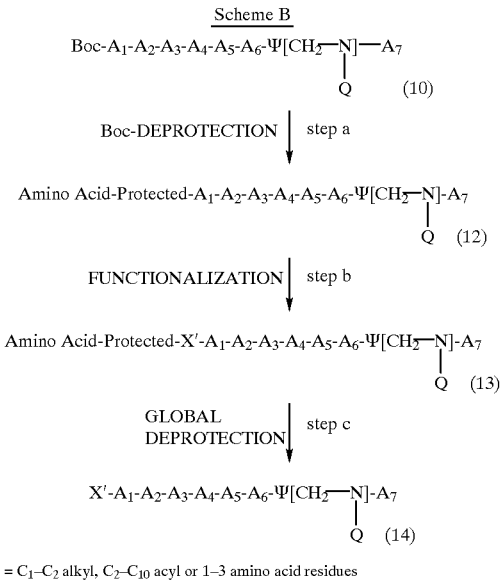

Scheme B

STEP A:

The Boc protecting group on A$_1$ of the appropriate Boc-A$_1$-A$_2$-A$_3$-A$_4$-A$_5$-A$_6$-Ψ[CH$_2$-N(Q)]-A$_7$ peptide amide of structure (10) or the Boc protecting group on A$_2$ of the appropriate Boc-A$_2$-A$_3$-A$_4$-A$_5$-A$_6$-Ψ[CH$_2$-N(Q)]-A$_7$ peptide amide of structure (10) is selectively removed by methods well known in the art to give the corresponding amino acid protected A$_1$-A$_2$-A$_3$-A$_4$-A$_5$-A$_6$-Ψ[CH$_2$-N(Q)]-A$_7$ peptide amide of structure (12) or A$_2$-A$_3$-A$_4$-A$_5$-A$_6$-Ψ[CH$_2$-N(Q)]-A$_7$ peptide amide of structure (12).

For example, the Boc protecting group on A$_1$ of the appropriate Boc-A$_1$-A$_2$-A$_3$-A$_4$-A$_5$-A$_6$-Ψ[CH$_2$-N(Q)]-A$_7$ peptide amide of structure (10) or the Boc protecting group on $A_2$ of the appropriate Boc-$A_2$-$A_3$-$A_4$-$A_5$-$A_6$-Ψ[$CH_2$-N(Q)]-$A_7$ peptide amide of structure (10) may then be removed to give the amino acid protected $A_1$-$A_2$-$A_3$-$A_4$-$A_5$-$A_6$-Ψ[$CH_2$-N(Q)]-$A_7$ peptide amide of structure (12) or the amino acid protected $A_2$-$A_3$-$A_4$-$A_5$-$A_6$-Ψ[$CH_2$-N(Q)]-$A_7$ peptide amide of structure (12) as described previously in step g.

STEP B:

The $A_1$ amine terminus, when $A_1$ is not a bond, of the appropriate amino acid protected $A_1$-$A_2$-$A_3$-$A_4$-$A_5$-$A_6$-Ψ[$CH_2$-N(Q)]-$A_7$ peptide amide of structure (12) or the $A_2$ amine terminus of the appropriate amino acid protected $A_2$-$A_3$-$A_4$-$A_5$-$A_6$-Ψ[$CH_2$-N(Q)]-$A_7$ peptide amide of structure (12) may be monoalkylated, dialkylated acylated, both alkylated and acylated or coupled with from 1–3 amino acid residues to give the corresponding amino acid protected mono-($C_1$–$C_6$ alkyl)-$A_1$-$A_2$-$A_3$-$A_4$-$A_5$-$A_6$-Ψ[$CH_2$-N(Q)]-$A_7$ peptide amide of structure (13), the corresponding di-($C_1$–$C_6$ alkyl)-$A_1$-$A_2$-$A_3$-$A_4$-$A_5$-$A_6$-Ψ[$CH_2$-N(Q)]-$A_7$ peptide amide of structure (13), the corresponding amino acid protected ($C_2$–$C_{10}$ acyl)-$A_1$-$A_2$-$A_3$-$A_4$-$A_5$-$A_6$-Ψ[$CH_2$-N(Q)]-$A_7$ peptide amide of structure (13), the corresponding ($C_1$-$C_6$ alkyl)-($C_2$–$C_{10}$ acyl)-$A_1$-$A_2$-$A_3$-$A_4$-$A_5$-$A_6$-Ψ[$CH_2$-N(Q)]-$A_7$ peptide amide of structure (13), the corresponding amino acid protected $A_8$-$A_1$-$A_2$-$A_3$-$A_4$-$A_5$-$A_6$-Ψ[$CH_2$-N(Q)]-$A_7$ peptide amide of structure (13), the corresponding amino acid protected $A_9$-$A_8$-$A_1$-$A_2$-$A_3$-$A_4$-$A_5$-$A_6$-Ψ[$CH_2$-N(Q)]-$A_7$ peptide amide of structure (13) or the corresponding amino acid protected $A_{10}$-$A_9$-$A_8$-$A_1$-$A_2$-$A_3$-$A_4$-$A_5$-$A_6$-Ψ[$CH_2$-N(Q)]-$A_7$ peptide amide of structure (13).

For example, the appropriate amino acid protected $A_1$-$A_2$-$A_3$-$A_4$-$A_5$-A6-Ψ[$CH_2$-N(Q)]-$A_7$ peptide amide of structure (12) or the appropriate amino acid protected $A_2$-$A_3$-$A_4$-$A_5$-$A_6$-Ψ[$CH_2$-N(Q)]-$A_7$ peptide amide of structure (12) is contacted with an equimolar amount of a suitable $C_1$–$C_6$ aldehyde, such as acetaldehyde and equimolar amount of a suitable reducing agent such as sodium cyanoborohydride. The reactants are typically contacted in a suitable organic solvent such as methanol. The reactantg are typically stirred together, maintaining a slightly acidic pH with dilute hydrochloride acid, for a period of time ranging from 2–24 hours and at a temperature range of from room temperature to reflux. The amino acid protected mono-($C_1$–$C_6$ alkyl)-$A_1$-$A_2$-$A_3$-$A_4$-$A_5$-$A_6$-Ψ[$CH_2$-N(Q)]-$A_7$ peptide amide of structure (13) and di-($C_1$–$C_6$ alkyl)-$A_1$-$A_2$-$A_3$-$A_4$-$A_5$-$A_6$-Ψ $CH_2$-N(Q))-$A_7$ peptide amide of structure (13) are recovered from the reaction zone by extractive methods as is known in the art. They may be separated and purified by chromatography.

Alternatively, the appropriate amino acid protected $A_1$-$A_2$-$A_3$-$A_4$-$A_5$-$A_6$-Ψ[$CH_2$-N(Q)]-$A_7$ peptide amide of structure (12) or the amino acid protected $A_2$-$A_3$-$A_4$-$A_5$-$A_6$-Ψ[$CH_2$-N(Q)]-$A_7$ peptide amide of structure (12) is contacted with an equimolar amount of a suitable $C_2$–$C_{10}$ acylating agent, such as acetic anhydride or acetyl chloride and a molar excess of a suitable non-nucleophilic base such as triethylamine. The reactants are typically contacted in a suitable organic solvent such as methylene chloride or dimethylformamide. The reactants are typically stirred together for a period of time ranging from 2–24 hours and at a temperature range of from room temperature to reflux. The amino acid protected ($C_2$–$C_{10}$ acyl)-$A_1$-$A_2$-$A_3$-$A_4$-$A_5$-$A_6$-Ψ[$CH_2$-N(Q)]-$A_7$ peptide amide of structure (13) is recovered from the reaction zone by extractive methods as is known in the art. It may be purified by chromatography.

Alternatively, the appropriate mono-($C_1$–$C_6$ alkyl)-$A_1$-$A_2$-$A_3$-$A_4$-$A_5$-$A_6$-Ψ[$CH_2$-N(Q)]-$A_7$ peptide amide of structure (13) may be acylated to give the corresponding amino acid protected ($C_1$–$C_6$ alkyl)-($C_2$–$C_{10}$ acyl)-$A_1$-$A_2$-$A_3$-$A_4$-$A_5$-$A_6$-Ψ[$CH_2$-N(Q)]-$A_7$ peptide amide of structure (13) as described previously in Scheme B, step b.

Alternatively, the appropriate amino acid protected $A_1$-$A_2$-$A_3$-$A_4$-$A_5$-$A_6$-Ψ[$CH_2$-N(Q)]-$A_7$ peptide amide of structure (12) is coupled with 1–3 amino acid residues using sequential condensation methods as is known in the art to give the corresponding amino acid protected $A_8$-$A_1$-$A_2$-$A_3$-$A_4$-$A_5$-$A_6$-Ψ[$CH_2$-N(Q)]-$A_7$ peptide amide of structure (13), the corresponding amino acid protected $A_9$-$A_8$-$A_1$-$A_2$-$A_3$-$A_4$-$A_5$-$A_6$-Ψ[$CH_2$-N(Q)]-$A_7$ peptide amide of structure (13) or the corresponding amino acid protected $A_{10}$-$A_9$-$A_8$-$A_1$-$A_2$-$A_3$-$A_4$-$A_5$-$A_6$-Ψ[$CH_2$-N(Q)]-$A_7$ peptide amide of structure (13).

In addition, the $A_8$ amine terminus of the appropriate amino acid protected $A_8$-$A_1$-$A_2$-$A_3$-$A_4$-$A_5$-$A_6$-Ψ[$CH_2$-N(Q)]-$A_7$ peptide amide of structure (13) may be monoalkylated, dialkylated, acylated or both alkylated and acylated to give the corresponding amino acid protected mono-($C_1$–$C_6$ alkyl)-$A_8$-$A_1$-$A_2$-$A_3$-$A_4$-$A_5$-$A_6$-Ψ[$CH_2$-N(Q)]-$A_7$ peptide amide of structure (13), the corresponding amino acid protected di-($C_1$–$C_6$ alkyl)-$A_8$-$A_1$-$A_2$-$A_3$-$A_4$-$A_5$-$A_6$-Ψ[$CH_2$-N(Q)]-$A_7$ peptide amide of structure (13), the corresponding amino acid protected ($C_2$–$C_{10}$ acyl)-$A_8$-$A_1$-$A_2$-$A_3$-$A_4$-$A_5$-$A_6$-Ψ[$CH_2$-N(Q)]-$A_7$ peptide amide of structure (13) and the corresponding amino acid protected ($C_1$–$C_6$ alkyl)-($C_2$–$C_{10}$ acyl)-$A_8$-$A_1$-$A_2$-$A_3$-$A_4$-$A_5$-$A_6$-Ψ[$CH_2$-N(Q)]-$A_7$ peptide amide of structure (13) as described previously in Scheme B, step b.

In addition, the $A_9$ amine terminus of the appropriate amino acid protected $A_9$-$A_8$-$A_1$-$A_2$-$A_3$-$A_4$-$A_5$-$A_6$-Ψ[$CH_2$-N(Q)]-$A_7$ peptide amide of structure (13) may be monoalkylated, dialkylated, acylated or both alkylated and acylated to give the corresponding amino acid protected Mono-($C_1$–$C_6$ alkyl)-$A_9$-$A_8$-$A_1$-$A_2$-$A_3$-$A_4$-$A_5$-$A_6$-Ψ[$CH_2$-N(Q)]-$A_7$ peptide amide of structure (13),the corresponding amino acid protected di-($C_1$–$C_6$ alkyl)-$A_9$-$A_8$-$A_1$-$A_2$-$A_3$-$A_4$-$A_5$-$A_6$-Ψ[$CH_2$-N(Q) ]-$A_7$ peptide amide of structure (13), the corresponding amino acid protected ($C_2$–$C_{10}$ acyl)-$A_9$-$A_8$-$A_1$-$A_2$-$A_3$-$A_4$-$A_5$-$A_6$-Ψ[$CH_2$-N(Q)]-$A_7$ peptide amide of structure (13) and the corresponding amino acid protected ($C_1$–$C_6$ alkyl)-($C_2$–$C_{10}$ acyl)-$A_9$-$A_8$-$A_1$-$A_2$-$A_3$-$A_4$-$A_5$-$A_6$-Ψ[$CH_2$-N(Q)]-$A_7$ peptide amide of structure (13) as described previously in Scheme B, step b.

In addition, the $A_{10}$ amine terminus of the appropriate amino acid protected $A_{10}$-$A_9$-$A_8$-$A_1$-$A_2$-$A_3$-$A_4$-$A_5$-$A_6$-Ψ[$CH_2$-N(Q)]-$A_7$ peptide amide of structure (13) may be monoalkylated, dialkylated, acylated or both alkylated and acylated to give the corresponding amino acid protected mono-($C_1$–$C_6$ alkyl)-$A_{10}$-$A_9$-$A_8$-$A_1$-$A_2$-$A_3$-$A_4$-$A_5$-$A_6$-Ψ[$CH_2$-N(Q) ]-$A_7$ peptide amide of structure (13),the corresponding amino acid protected di-($C_1$–$C_6$ alkyl)-$A_{10}$-$A_9$-$A_8$-$A_1$-$A_2$-$A_3$-$A_4$-$A_5$-$A_6$-Ψ[$CH_2$-N(Q)]-$A_7$ peptide amide of structure (13), the corresponding amino acid protected ($C_2$–$C_{10}$ acyl)-$A_{10}$-$A_9$-$A_8$-$A_1$-$A_2$-$A_3$-$A_4$-$A_5$-$A_6$-Ψ[$CH_2$-N(Q)]-$A_7$ peptide amide of structure (13) and the corresponding amino acid protected ($C_1$–$C_6$ alkyl)-($C_2$–$C_{10}$ acyl)-$A_{10}$-$A_9$-$A_8$-$A_1$-$A_2$-$A_3$-$A_4$-$A_5$-$A_6$-Ψ[$CH_2$-N(Q) ]-$A_7$ peptide amide of structure (13) as described previously in Scheme B, step b.

STEP C:

The various protecting groups on the amino acids residues on the compounds of Formula 1 described in Scheme B, step b may be removed by a global deprotection as described previously in Scheme A, step i.

Starting materials for use in Scheme B are readily available to one of ordinary skill in the art.

The following example presents a typical synthesis as described in Scheme S. This example is understood to be illustrative only an is not intended to limit the scope of the present invention in any way.

EXAMPLE 2

CH$_3$-C(O)-Asp-Ser-Phe-Val-Gly-Leu-Ψ[CH$_2$-N(CH$_2$CF$_3$)]-Leu(NH2) SEQ ID NO:8.

Step a: Asp(OBn)-Ser(OBn)-Phe-Val-Gly-Leu-Ψ[CH$_2$-N(CH$_2$CF$_3$)]-Leu(NH$_2$)•hydrochloride salt - SEQ ID NO:9.

Mix Boc-Asp(OBn)-Ser(OBn)-Phe-Val-Gly-Leu-Ψ[CH$_2$-N(CH$_2$CF$_3$)]-Leu(NH$_2$) (1.09 g, 0.980 mmol), 4 N hydrochloric acid in dioxane. Stir at room temperature for 1 hour. Evaporate the solvent invacuo to give the title compound.

Step b: CH$_3$-C(O)-Asp(OBn)-Ser(OBn)-Phe-Val-Gly-Leu-Ψ[CH$_2$-NH$_2$CF$_3$)]-Leu(NH$_2$) - SEQ ID NO: 10.

Dissolve Asp(OBn)-Ser(OBn)-Phe-Val-Gly-Leu-Ψ[CH$_2$-N(CH$_2$CF$_3$)]-Leu(NH2)•hydrochloride salt (2.30 g, 2.27 mmol) in dimethylformamide (15 mL) and treat with triethylamine (0.7 mL, 5 mmol) followed by acetic anhydride (0.2 mL, 2.27 mmol) and stir at room temperature overnight. Evaporate the solvent in vacuo, partition between methylene chloride and brine. Separate the organic phase, dry (MgSO$_4$), evaporate the solvent invacuo and purify by chromatography to give the title compound.

Step c: CH$_3$-C(O)-Asp-Ser-Phe-Val-Gly-Leu-Ψ[CH$_2$-N(CH$_2$CF$_3$)]-Leu(NH2) - SEQ ID NO:8.

Dissolve CH$_3$-C(O)-Asp(OBn)-Ser(OBn)-Phe-Val-Gly-Leu-Ψ[CH$_2$-N(CH$_2$CF$_3$)]-Leu(NH2) (106 mg, 0.1 mmol) in hydrogen fluoride and anisole. Stir for 1 hour at 0° C. Allow the solvent to evaporate to give the title compound.

The following compounds can be prepared in a similar fashion to that described in Example 2:

Ac-Asp-Ser-Phe-Val-β-Ala-Leu-Ψ[CH$_2$-N(CH$_2$CF$_3$)]-Phe(NH$_2$) SEQ ID NO:11.

The compounds of Formula I wherein A$_7$ is an amino acid residue as previously described wherein the —COOH group is replaced with a —CONH$_2$ group and the reduced amide bond substitution represented by —Ψ[CH$_2$-N(Q)] is located between amino acid residues of A$_1$–A$_2$, wherein A$_1$ is not a bond, A$_2$–A$_3$, A$_3$–A$_4$, A$_4$–A$_5$ or A$_5$–A$_6$ can be prepared by teohniques and procedures well known and appreciated by one of ordinary skill in the art. General synthetic procedures for preparing these compounds is set forth in Scheme C. In Scheme C, all substituents unless otherwise indicated are as previously defined.

Scheme C provides a general synthetic procedure for preparing the compounds of Formula I wherein A$_7$ is an amino acid residue as previously described wherein the —COOH group is replaced with a —CONH$_2$ and the reduced amide bond substitution represented by —Ψ[CH$_2$-N(Q)] is located between amino acid residues of A$_1$–A$_2$, wherein A$_1$ is not a bond, A$_2$–A$_3$, A$_3$–A$_4$, A$_4$–A$_5$ or A$_5$–A$_6$.

In step a, the appropriate Boc-A$_n$ amino acid of structure (15), wherein n represents an integer 1–5, is coupled with an appropriate A$_{n+1}$ amino acid methyl ester of structure (16), wherein n is as previously defined, to give the corresponding Boc-A$_n$-A$_{n+1}$ peptide methyl ester of structure (17) as described previously in Scheme A, step a.

The selection of proper amino acid starting materials is based on the desired placement of the reduced amide bond in the final compound of Formula I. For example, if the reduced amide bond is to be located between amino acid residues A$_3$–A$_4$, the proper Boc-A$_n$ amino acid of structure (15) would be one wherein n=3 and the proper A$_{n+1}$ amino acid methyl ester of structure (16) would be one wherein n+1=4.

In step b, the amide functionality of the appropriate Boc-A$_n$-A$_{n+1}$ peptize methyl ester of structure (17) is thioamidated to give the corresponding Boc-A$_n$-Ψ[C(S)-NH]-A$_{n+1}$ peptide methyl ester of structure (18) as described previously in Scheme A, step b.

In step c, the thioamide functionality of the appropriate Boc-A$_n$-Ψ[C(S)-NH]-A$_{n+1}$ peptide methyl ester of structure (18) is reduced to give the corresponding Boc-A$_n$-Ψ[CH$_2$-NH]-A$_{n+1}$ peptide methyl ester of structure (19) as described previously in Scheme A, step c.

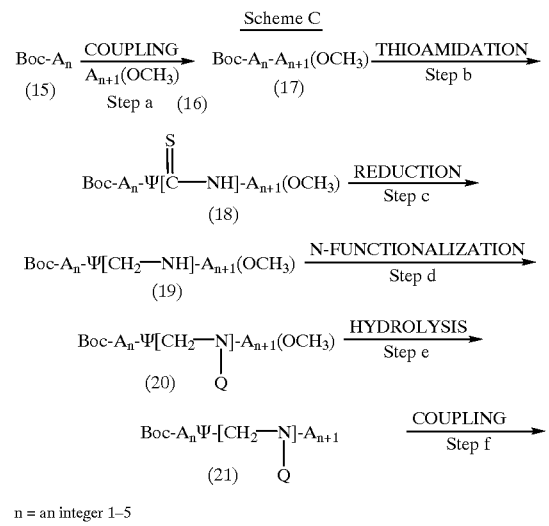

Scheme C n = an integer 1–5

In step d, the amine functionality of the appropriate Boc-A$_n$-Ψ[CH$_2$-NH]-A$_{n+1}$ peptide methyl ester of structure (19) is functionalized to give the corresponding Boc-A$_n$-Ψ[CH$_2$-N(Q)]-A$_{+1}$ peptide methyl ester of structure (20) as described previously in Scheme A, step d.

In step e, the methyl ester functionality of the appropriate Boc-A$_n$-Ψ[CH$_2$-N(Q)]-A$_{n+1}$ peptide methyl ester of structure (20) is hydrolyzed to give the corresponding Boc-A$_n$-Ψ[CH$_2$-N(Q)]-A$_{n+1}$ peptide of structure (21) as described previously in Scheme A, step e.

In step f, the appropriate Boc-A$_1$-Ψ[CH$_2$-N(Q)]-A$_{n+1}$ peptide of structure (21) is then coupled with the appropriate amino acids of peptides to give the corresponding Boc-protected compound of Formula I wherein the reduced amide bond is located between amino acid residues A$_1$–A$_2$, wherein A$_1$ is not a bond, A$_2$–A$_3$, A$_3$–A$_4$, A$_4$–A$_5$ or A$_5$–A$_6$ as described previously in Scheme A, step h.

For example, if the reduced amide bond is located between amino acid residues A$_1$ and A$_2$, wherein A$_1$ is not a bond, the appropriate Boc-A$_n$-Ψ[CH$_2$-N(Q)]-A$_{n+1}$ peptide of structure (21), as represented by Boc-A$_1$-Ψ[CH$_2$-N(Q)]-A$_2$, is coupled with an appropriately protected preformed A$_3$-A$_4$-A$_5$-A$_6$-A$_7$ peptide amide to give the corresponding Boc-A$_1$-Ψ[CH$_2$-N(Q)]-A$_2$-A$_3$-A$_4$-A$_5$-A$_6$-A$_7$ peptide amide.

If the reduced amide bond is located between amino acid residues A$_2$ and A$_3$, the appropriate Boc-A$_n$-Ψ[CH$_2$-N(Q)]-A$_{n+1}$ peptide of structure (21), as represented by Boc-A$_2$-Ψ[CH$_2$-N(Q)]-A$_3$, is coupled with an appropriately protected preformed A$_4$-A$_5$-A$_6$-A$_7$ peptide amide to give the corresponding Boc-A$_2$-Ψ[CH$_2$-N(Q)]-A$_3$-A$_4$-A$_5$-A$_6$-A$_7$ peptide amide. The Boc-protecting group on amino acid A$_2$ is then removed to give the corresponding A$_2$-Ψ[CH$_2$-N(Q)]-A$_3$-A$_4$-A$_5$-A$_6$-A$_7$ peptide amide which is then optionally coupled with the appropriate Boc-A$_1$ amino acid, wherein A$_1$ is not a bond, give the corresponding Boc-A$_1$-A$_2$-Ψ[CH$_2$-N(Q)]-A$_3$-A$_4$-A$_5$-A$_6$-A$_7$ peptide amide.

If the reduced amide bond is located between amino acid residues $A_3$ and $A_4$, the appropriate Boc-$A_n$-Ψ[$CH_2$-N(Q)]-$A_{n+1}$ peptide of structure (21), as represented by Boc-$A_3$-Ψ[$CH_2$-N(Q)]-$A_4$, is coupled with an appropriately protected preformed $A_5$-$A_6$-$A_7$ peptide amide to give the corresponding Boc-$A_3$-Ψ[$CH_2$-N(Q)]-$A_4$-$A_5$-$A_6$-$A_7$ peptide amide. The Boc-protecting group on amino acid $A_3$ is then removed to give the corresponding $A_3$-Ψ[$CH_2$-N(Q)]-$A_4$-$A_5$-$A_6$-$A_7$ peptide amide which is then coupled with the appropriate Boc-$A_2$ amino acid to give the corresponding Boc-$A_2$-$A_3$-Ψ[$CH_2$-N(Q)]-$A_4$-$A_5$-$A_6$-$A_7$ peptide amide. The Boc-protecting group on amino acid $A_2$ is then removed to give the corresponding $A_2$-$A_3$-Ψ[$CH_2$-N(Q)]-$A_4$-$A_5$-$A_6$-$A_7$ peptide amide which is then optionally coupled with the appropriate Boc-$A_1$ amino acid, wherein $A_1$ is not a bond, to give the corresponding Boc-$A_1$-$A_2$-$A_3$-Ψ[$CH_2$-N(Q)]-$A_4$-$A_5$-$A_6$-$A_7$ peptide amide.

If the reduced amide bond is located between amino acid residues $A_4$ and $A_5$, the appropriate Boc-$A_n$-Ψ[$CH_2$-N(Q)]-$A_{n+1}$ peptide of structure (21), as represented by Boc-$A_4$-Ψ[$CH_2$-N(Q)]-$A_5$, is coupled with an appropriately protected preformed $A_6$–$A_7$ peptide amide to give the corresponding Boc-$A_4$-Ψ[$CH_2$-N(Q)]-$A_5$-$A_6$-$A_7$ peptide amide. The Boc-protecting group on amino acid $A_4$ is then removed to give the corresponding $A_4$-Ψ[$CH_2$-N(Q)]-$A_5$-$A_6$-$A_7$ peptide amide which is then coupled with the appropriate Boc-$A_3$ amino acid to give the corresponding Boc-$A_3$-$A_4$-Ψ[$CH_2$-N(Q) ]-$A_5$-$A_6$-$A_7$ peptide amide. The Boc-protecting group on amino acid $A_3$ is then removed to give the corresponding $A_3$-$A_4$-Ψ[$CH_2$-N(Q)]-$A_5$-$A_6$-$A_7$ peptide amide which is then coupled with the appropriate Boc-$A_2$ amino acid to give the corresponding Boc-$A_2$-$A_3$-$A_4$-Ψ[$CH_2$-N(Q)]-$A_5$-$A_6$-$A_7$ peptide amide. The Boc-protecting group on amino acid $A_2$ is then removed to give the corresponding $A_2$-$A_3$-$A_4$-Ψ[$CH_2$-N(Q)]-$A_5$-$A_6$-$A_7$ peptide amide which is then optionally coupled with the appropriate Boc-$A_1$ amino acid, wherein $A_1$ is not a bond, to give the corresponding Boc-$A_1$-$A_2$-$A_3$-$A_4$-Ψ[$CH_2$-N(Q) ]-$A_5$-$A_6$-$A_7$ peptide amide.

If the reduced amide bond is located between amino acid residues $A_5$ and $A_6$, the appropriate Boc-$A_n$-Ψ[$CH_2$-N(Q)]-$A_{n+1}$ peptide of structure (21), as represented by Boc-$A_5$-Ψ[$CH_2$-N(Q)]-$A_6$, is coupled with an appropriately protected $A_7$ amino acid amide to give the corresponding Boc-$A_5$-Ψ[$CH_2$-N(Q)]-$A_6$-$A_7$ peptide amide. The Boc-protecting group on amino acid $A_5$ is then removed to give the corresponding $A_5$-Ψ[$CH_2$-N(Q)]-$A_6$-$A_7$ peptide amide which is then coupled with the appropriate Boc-$A_4$ amino acid to give the corresponding Boc-$A_4$-$A_5$-Ψ[$CH_2$-N(Q)]-$A_6$-$A_7$ peptide amide. The Boc-protecting group on amino acid $A_4$ is then removed to give the corresponding $A_4$-$A_5$-Ψ[$CH_2$-N(Q)]-$A_6$-$A_7$ peptide amide which is then coupled with the appropriate Boc-$A_3$ amino acid to give the corresponding Boc-$A_3$-$A_4$-$A_5$-Ψ[$CH_2$-N(Q)]-$A_6$-$A_7$ peptide amide. The Boc-protecting group on amino acid $A_3$ is then removed to give the corresponding $A_3$-$A_4$-$A_5$-Ψ[$CH_2$-N(Q)]-$A_6$-$A_7$ peptide amide which is then coupled with the appropriate Boc-$A_2$ amino acid to give the corresponding Boc-$A_2$-$A_3$-$A_4$-$A_5$-Ψ[$CH_2$-N(Q)]-$A_6$-$A_7$ peptide amide. The Boc-protecting group on amino acid $A_2$ is then removed to give the corresponding $A_2$-$A_3$-$A_4$-$A_5$-Ψ[$CH_2$-N(Q) ]-$A_6$-$A_7$ peptide amide which is then optionally coupled with the appropriate Boc-$A_1$ amino acid, wherein $A_1$ is not a bond, to give the corresponding BoC-$A_1$-$A_2$-$A_3$-$A_4$-$A_5$-Ψ[$CH_2$-N(Q)]-$A_6$-$A_7$ peptide amide.

If no further functionalization is desired, the protecting groups are removed from the various Boc-protected compounds of Formula I wherein the reduced amide bond is located between amino acid residues $A_1$–$A_2$, wherein $A_1$ is not a bond, $A_2$–$A_3$, $A_3$–$A_4$, $A_4$–$A_5$ or $A_5$–$A_6$ to give the corresponding compound of Formula I wherein the reduced amide bond is located between amino acid residues $A_1$–$A_2$, wherein $A_1$ is not a bond, $A_2$–$A_3$, $A_3$–$A_4$, $A_4$–$A_5$ or $A_5$–$A_6$ as described previously in Scheme A, step i.

If further functionalization is desired, the $A_1$ amine terminus or the $A_2$ amine terminus of the appropriate compounds of Formula I wherein the reduced amide bond is located between amino acid residues $A_1$–$A_2$, wherein $A_1$ is not a bond, $A_2$–$A_3$, $A_3$–$A_4$, $A_4$–$A_5$ or $A_5$–$A_6$ may be monoalkylated, dialkylated, acylated, both alkylated and acylated or coupled with 1–3 amino acid residues to give the corresponding amino acid protected mono-($C_1$–$C_6$ alkyl)-compounds of Formula I wherein the reduced amide bond is located between amino acid residues $A_1$–$A_2$, wherein $A_1$ is not a bond, $A_2$–$A_3$, $A_3$–$A_4$, $A_4$–$A_5$ or $A_5$–$A_6$, the corresponding amino acid protected di-($C_1$–$C_6$ alkyl)-compounds of Formula I wherein the reduced amide bond is located between amino acid residues $A_1$–$A_2$, wherein $A_1$ is not a bond, $A_2$–$A_3$, $A_3$–$A_4$, $A_4$–$A_5$ or $A_5$–$A_6$, the corresponding amino acid protected ($C_2$–$C_{10}$ acyl)-compounds of Formula I wherein the reduced amide bond is located between amino acid residues $A_1$–$A_2$, wherein $A_1$ is not a bond, $A_2$–$A_3$, $A_3$–$A_4$, $A_4$–$A_5$ or $A_5$–$A_6$, the corresponding amino acid protected ($C_1$–$C_6$ alkyl)-($C_2$–$C_{10}$ acyl)-compounds of Formula I wherein the reduced amide bond is located between amino acid residues $A_1$–$A_2$, wherein $A_1$ is not a bond, $A_2$–$A_3$, $A_3$–$A_4$, $A_4$–$A_5$ or $A_5$–$A_6$, the corresponding $A_8$-compounds of Formula I wherein the reduced amide bond is located between amino acid residues $A_1$–$A_2$, wherein $A_1$ is not a bond, $A_2$–$A_3$, $A_3$–$A_4$, $A_4$–$A_5$ or $A_5$–$A_6$, the corresponding $A_9$-$A_8$-compounds of Formula I wherein the reduced amide bond is located between amino acid residues $A_1$–$A_2$, wherein $A_1$ is not a bond, $A_2$–$A_3$, $A_3$–$A_4$, $A_4$–$A_5$ or $A_5$–$A_6$, the corresponding $A_{10}$-$A_9$-$A_8$-compounds of Formula I wherein the reduced amide bond is located between amino acid residues $A_1$–$A_2$, wherein $A_1$ is not a bond, $A_2$–$A_3$, $A_3$–$A_4$, $A_4$–$A_5$ or $A_5$–$A_6$, the corresponding $A_8$ amine terminus monoalkylated, dialkylated, acylated, both alkylated and acylated $A_8$-compounds of Formula I wherein the reduced amide bond is located between amino acid residues $A_1$–$A_2$, wherein $A_1$ is not a bond, $A_2$–$A_3$, $A_3$–$A_4$, $A_4$–$A_5$ or $A_5$–$A_6$, the corresponding $A_9$ amino terminus monoalkylated, dialkylated, acylated, both alkylated and acylated $A_9$-$A_8$-compounds of Formula I wherein the reduced amide bond is located between amino acid residues $A_1$–$A_2$, wherein $A_1$ is not a bond, $A_2$–$A_3$, $A_3$–$A_4$, $A_4$–$A_5$ or $A_5$–$A_6$, the corresponding $A_{10}$ amino terminus monoalkylated, dialkylated, acylated, both alkylated and acylated $A_{10}$-$A_9$-$A_8$-compounds of Formula I wherein the reduced amide bond is located between amino acid residues $A_1$–$A_2$, wherein $A_1$ is not a bond, $A_2$–$A_3$, $A_3$–$A_4$, $A_4$–$A_5$ or $A_5$–$A_6$ as described previously in Scheme B.

Starting materials for use in Scheme C are readily availiable to one of ordinary skill in the art.

The following examples present typical syntheses as described in Scheme C. These example are understood to be illustrative only and are not intended to limit the scope of the present invention in any way.

EXAMPLE 3

Asp-Ser-PheΨ[$CH_2$-N($CH_2CF_2H$)]-Val-Gly-Leu-Met ($NH_2$) SEQ ID NO:12.

Step a.! Boc-Phe-Val(OCH₃)

Mix Boc-Phe (5.31 g, 20 mmol), Val(OMe) hydrochloride (3.36 g, 20 mmol), 1-(3-dimethylaminopropyl)-3- ethylcarbodiimide hydrochloride (EDC) (3.83 g, 20 mmol), 1-hydroxybenzotriazole hydrate (3.06 g, 20 mmol), diisopropylethylamine (3.5 mL, 20 mmol) and methylene chloride (40 mL). Stir at room temperature under a nitrogen atmosphere until the reaction is complete. Dilute with ethyl acetate and wash with 1 N hydrochloric acid, saturated sodium hydrogen carbonate and brine. Dry (MgSO$_4$) and evaporate the solvent invacuo to give the title compound.

Step b: Boc-PheΨ[C(S)-NH$_2$]-Val(OCH$_3$)

Mix Boc-Phe-Val(OCH$_3$) (378 mg, 1 mmol), 2,4-bis(phenylthio)-1,3-dithio-2,4-diphosphetane-2,4-dithione (0.45 g, 1,1 mmol) and anhydrous tetrahydrofuran (3 mL). Stir at room temperature under a nitrogen atmosphere for 8 hours. Dilute with ethyl acetate and wash with 1 N hydrochloric acid, saturated sodium hydrogen carbonate and brine. Dry (MgSO$_4$) and evaporate the solvent invacuo to give the title compound.

Step c: Boc-PheΨ[CH$_2$-NH$_2$]-Val(OCH$_3$)

Dissolve Boc-PheΨ[C(S)-NH$_2$]-Val(OCH$_3$) (394 mg, 1 mmol) in a mixture of 1:1 tetahydofuran/methanol (10 mL). Add nickel chloride hexahydrate (NiCl$_2$•6H$_2$O) (1.9 g, 8 mmol) and cool in an ice bath. Add sodium borohydride (0.91 g, 24 mmol) and stir at room temperature under a nitrogen atmosphere for 20 minutes. Filter and evaporate the solvent in vacuo to give the title compound.

Step d: Boc-PheΨ[CH$_2$-N(CH$_2$CF$_2$H)]-Val(OCH$_3$)

Mix Boc-PheΨ[CH$_2$-NH$_2$]-Val(OCH$_3$) (158 mg, 0.435 mmol), 2,2-difluoroethyl trifluoromethanesulfonate (372 mg, 1.74 mmol), triethylamine (0.06 mL, 0.435 mmol) and benzene (2 mL). Heat at reflux for 7 days, occasionally adding additional 2,2-difluoroethyl trifluoromethanesulfonate and triethylamine. Cool to room temperature, wash with 1 N hydrochloric acid then saturated sodium hydrogen carbonate and brine. Dry (MgSO$_4$) and evaporate the solvent in vacuo to give the title compound.

Step e: Boc-PheΨ[CH$_2$-N(CH$_2$CF$_2$H)]-Val

Dissolve Boc-PheΨ[CH$_2$-N(CH$_2$CF$_2$H)]-Val(OCH$_3$) (452 mg, 1.055 mmol) in ethanol (10 mL) and add 1 N sodium hydroxide (10 mL). Stir at room temperature overnight. Dilute with water and acidify with 1 N hydrochloric acid. Extract into ethyl acetate, dry (MgSO$_4$) and evaporate the solvent in vacuo to give the title compound.

Step f: Boc-Asp(O-β-Chxl)-Ser(OBn)-PheΨ[CH$_2$-N(CH$_2$CF$_2$H)]-Val-Gly-Leu-Met(NH$_2$)—SEQ ID NO:13.

Mix Boc-Leu (4.98 g, 20 mmol), Met(OMe) hydrochloride (4.0 g, 20 mmol), 1-(3-dimethylaminopropyl)-3-ethylcarbodiimide hydrochloride (EDC) (3.83 g, 20 mmol), 1-hydroxybenzotriazole hydrate (3.06 g, 20 mmol), diisopropylethylamine (3.5 mL, 20 mmol) and methylene chloride (40 mL). Stir at room temperature under a nitrogen atmosphere until the reaction is complete. Dilute with ethyl acetate and wash with 1 N hydrochloric acid, saturated sodium hydrogen carbonate and brine. Dry (MgSO$_4$) and evaporate the solvent in vacuo to give Boc-Leu-Met(OMe).

Dissolve Boc-Leu-Met(OMe) (397 mg, 1.055 mmol) in ethanol (10 mL) and add 1 N sodium hydroxide (10 mL). Stir at room temperature overnight. Dilute with water and acidify with 1 N hydrochloric acid. Extract into ethyl acetate, dry (MgSO$_4$) and evaporate the solvent in vacuo to give Boc-Leu-Met.

Dissolve Boc-Leu-Met (351 mg, 0.97 mmol) in ethyl acetate (10 mL) and cool to −20° C. Add triethylamine (0.15 mL, 1 mmol) and isobutylchloroformate (0.13 mL, 1 mmol). Stir at −20° C. for 20 minutes. Bubble ammonia gas into the reaction mixture at −20° C. for 10 minutes then allow to warm to room temperature overnight. Wash with brine and dry (MgSO$_4$). Evaporate the solvent in vacuo to give Boc-Leu-Met(NH$_2$).

Mix Boc-Leu-Met(NH$_2$) (351 mg, 0.97 mmol), 4 N hydrochloric acid in dioxane. Stir at room temperature for 1 hour. Evaporate the solvent in vacuo to give Leu-Met(NH$_2$) hydrochloride.

Mix Boc-Gly (3.5 g, 20 mmol), Leu-Met(NH$_2$) hydrochloride (5.98 g, 20 mmol), 1-(3-dimethylaminopropyl)-3-ethylcarbodiimide hydrochloride (EDC) (3.83 g, 20 mmol), 1-hydroxybenzotriazole hydrate (3.06 g, 20 mmol), diisopropylethylamine (3.5 mL, 20 mmol) and methylene chloride (40 mL). Stir at room temperature under a nitrogen atmosphere until the reaction is complete. Dilute with ethyl acetate and wash with 1 N hydrochloric acid, saturated sodium hydrogen carbonate and brine. Dry (MgSO$_4$) and evaporate the solvent in vacuo to give Boc-Cly-Leu-Met(NH$_2$).

Mix Boc-Gly-Leu-Met(NH$_2$) (1.09 g, 2.69 mmol), 4 N hydrochloric acid in dioxane. Stir at room temperature for 1 hour. Evaporate the solvent in vacuo to give Gly-Leu-Met(NH$_2$) hydrochloride.

Mix Roc-PheΨ[CH$_2$-N(CH$_2$CF$_2$H)]-Val (7.58 g, 20 mmol), Gly-Leu-Met(NH$_2$) hydrochloride (7.12 g, 20 mmol), 1-(3-dimethylaminopropyl)-3-ethylcarbodiimide hydrochloride (EDC) (3.83 g, 20 mmol), 1-hydroxybenzotriazole hydrate (3.06 g, 20 mmol), diisopropylethylamine (3.5 mL, 20 mmol) and methylene chloride (40 mL). Stir at room temperature under a nitrogen atmosphere until the reaction is complete. Dilute with ethyl acetate and wash with 1 N hydrochloric acid, saturated sodium hydrogen carbonate and brine. Dry (MgSO$_4$) and evaporate the solvent in vacuo to give Boc-PheΨ[CH$_2$-N(CH$_2$CF$_2$H)]-Val-Gly-Leu-Met(NH$_2$)—SEQ ID NO:14.

Mix Boc-PheΨ[CH$_2$-N(CH$_2$CF$_2$H)]-Val-Gly-Lau-Met(NH$_2$) SEQ ID NO:14, (1.09 g, 1.52 mmol), 4 N hydrochloric acid in dioxane. Stir at room temperature for 1 hour. Evaporate the solvent in vacuo to give PheΨ[CH$_2$-N(CH$_2$CF$_2$H)]-Val-Cldy-Leu-Met(NH$_2$) hydrochloride.

Mix Boc-Ser(OBn) (5.9g, 20 mmol), PheΨ[CH$_2$-N(CH$_2$CF$_2$H) ]-Val-Gly-Leu-Met(NH$_2$) hydrochloride, SEQ ID NO:15, (13.04 g, 20 mmol), 1-(3-dimethylaminopropyl)-3-ethylcarbodiimide hydrochloride (EDC) (3.83 g, 20 mmol), 1-hydroxybenzotriazole hydrate (3.06 g, 20 mmol), diisopropylethylamine (3.5 mL, 20 mmol) and methylene chloride (40 mL). Stir at room temperature under a nitrogen atmosphere until the reaction is complete. Dilute with ethyl acetate and wash with 1 N hydrochloric acid, saturated sodium hydrogen carbonate and brine. Dry (MgSO$_4$) and evaporate the solvent in vacuo to give Boc-Ser(OBn)-PheΨ[CH$_2$-N(CH$_2$CF$_2$H)]-Val-Gly-Leu-Met(NH$_2$) SEQ ID NO:16.

Mix Boc-Ser(OBn)-PheΨ[CH$_2$-N(CH$_2$CF$_2$H)]-Val-Gly-Leu-Met(NH$_2$), SEQ ID NO:16, (1.09 g, 1.22 mmol), 4 N hydrochloric acid in dioxane. Stir at room temperature for 1 hour. Evaporate the solvent in vacuo to give Ser(OBn)-PheΨ[CH$_2$-N(CH$_2$CF$_2$H)]-Val-Gly-Leu-Met(NH$_2$) hydrochloride, SEQ ID NO:17. Mix Boc-Asp(O-β-Chxl) (5.94 g, 20 mmol), Ser(OBn)-PheΨ[CH$_2$-N(CH$_2$CF$_2$H)]-Val-Gly-Leu-Met(NH$_2$) hydrochloride, SEQ ID NO:17, (16.58 g, 20 mmol), 1-(3-dimethylaminopropyl)-3-ethylcarbodiimide hydrochloride (EDC) (3.83 g, 20 mmol), 1-hydroxybenzotriazole hydrate (3.06 g, 20 mmol), diisopropylethylamine (3.5 mL, 20 mmol) and methylene chloride (40 mL). Pier at room temperature under a nitrogen atmosphere until the reaction is complete. Dilute with ethyl acetate and wash with 1 N hydrochloric acid, saturated sodium hydrogen carbonate and brine. Dry (MgSO$_4$) and evaporate the solvent in vacuo to give the title compound.

Scheme A, step i: Asp-Ser-PheΨ[CH$_2$-N(CH$_2$CF$_2$H)]-Val-Gly-Leu-Met(NH$_2$)—SEQ ID NO:12.

Suspend Boc-Asp(O-β-Chxl)-Ser(OBn)-PheΨ[CH$_2$-N(CH$_2$CF$_2$H)]-Val-Gly-Leu-Met(NH$_2$), SEQ ID NO;13, (107 mg, 0.1 mmol) in hydrogen fluoride and anisoles Stir for 1 hour at 0° C. Allow the solvent to evaporate to give the title compound.

The following compounds can be prepared in a similar fashion to that described above in Example 3:

Asp-Ser-PheΨ[CH$_2$-N(CH$_2$CF$_3$)]-Val-Gly-Leu-Leu(NH$_2$)—SEQ ID NO:18;

Asp-Ser-PheΨ[CH$_2$-N(CH$_2$CF$_3$)]-Val-β-Ala-Leu-Phe(NH$_2$) - SEQ ID NO:19; and pyroGlu-PheΨ[CH$_2$-N(CH$_2$CF$_3$)]-Phe-Gly-Leu-Met(NH$_2$)—SEQ ID NO:20.

The compounds of Formula I wherein A$_7$ is an amino acid residue as previously described wherein the —COOH group is replaced with a —CH$_2$OH group and the reduced amide bond substitution represented by —Ψ[CH$_2$-N(Q)] is located between amino acid residues of A$_6$–A$_7$ can be prepared by techniques and procedures well known and appreciated by one of ordinary skill in the art. General synthetic procedures for preparing these compounds are set forth in Scheme D. In Scheme D, all substituents unless otherwise indicated are as previously defined.

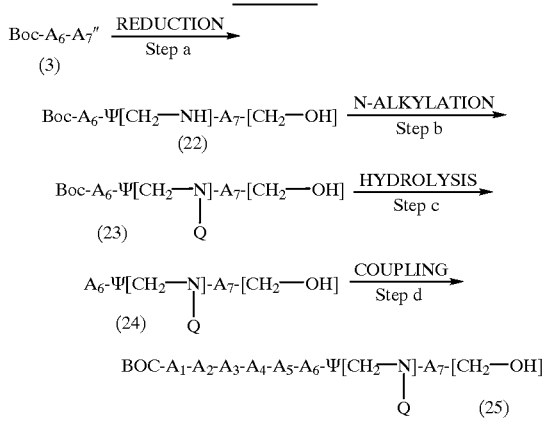

A$_7''$ = A$_7$ as previously defined wherein the ——COOH group is replaced with ——C(O)OCH$_3$ Scheme C provides a general synthetic procedure for preparing the compounds of Formula I wherein A$_7$ is an amino acid residue as previously described wherein the —COOH group is replaced with a —CH$_2$OH and the reduced amide bond substitution represented by —Ψ[CH$_2$-N(Q)] is located between amino acid residues of A$_6$–A$_7$.

In step a, the appropriate Boc-A$_6$–A$_7$ peptide methyl ester of structure (3) is reduced to give the corresponding Boc-A$_6$-[CH$_2$-NH]-A$_7$-Ψ[CH$_2$OH] peptide of structure (22).

For example, the appropriate Boc-A$_6$–A$_7$ peptide methyl ester of structure (3) is contacted with a molar excess of an appropriate reducing agent such as Red-A1. The reactants are typically contacted in a suitable aprotic organic solvent such as benzene. The reactants are typiCally stirred together for a period of time ranging from 5 minutes to 10 hours and at a temperature range of from room temperature to reflux. The Boc-A$_6$-Ψ[CH$_2$-NH]-A$_7$[CH$_2$OH] peptide of structure (22) is recovered from the reaction by acidification followed by extractive methods as is known in the art. It may be purified by chromatography.

In step b, the amino functionality of the appropriate Boc-A$_6$-Ψ[CH$_2$-NH]-A$_7$(CH$_2$OH] peptide of structure (22) is functionalized to give the corresponding Boc-A$_6$-Ψ[CH$_2$-N(Q)]-A$_7$[CH$_2$OH] peptide of structure (23) as described previously in Scheme A, step d.

In step c, the Boc-protecting group on the A$_6$ amino acid residue of the appropriate Boc-A$_6$-Ψ[CH$_2$-N(Q)]-A$_7$[CH$_2$OH] peptide of structure (23) is hydrolyzed to give the corresponding A$_6$-Ψ[CH$_2$-N(Q)]-A$_7$(CH$_2$OH) peptide of structure (24) as described previously in Scheme A, step g.

In step d, the A$_6$-Ψ[CH$_2$-N(Q)]-A$_7$[CH$_2$OH] peptide of structure (24) is coupled to give the corresponding Boc-A$_1$-A$_2$-A$_3$-A$_4$-A$_5$-A$_6$-Ψ[CH$_2$-N(Q)J-A$_7$[CH$_2$OH] peptide alcohol of structure (25) as described previously in Scheme A, step h.

If no further functionalizatiQn is desired, the Boc protecting group on A$_1$, wherein A$_1$ is not a bond, or the Boc protecting group on A$_2$, wherein A$_1$ is a bond, and various other protecting groups on amino acids A$_1$–A$_7$, wherein A$_1$ is not a bond, or amino acids A$_2$–A$_7$, wherein A$_1$ is a bond, of the appropriate Boc-A$_1$-A$_2$-A$_3$-A$_4$-A$_5$-A$_6$-Ψ[CH$_2$-N(Q)]-A$_7$[CH$_2$OH] peptide alcohol of structure (25) are removed by methods well known in the art tQ give the corresponding A$_1$-A$_2$-A$_3$-A$_4$-A$_5$-A$_6$-Ψ[CH$_2$-N(Q)]-A$_7$[CH$_2$OH] peptide alcohol of Formula I, wherein A$_1$ is not a bond, the corresponding A$_2$-A$_3$-A$_4$-A$_5$-A$_6$-Ψ[CH$_2$-N(Q)]-A$_7$[CH$_2$OH] peptide alcohol of Formula I, wherein A$_1$ is a bond as described previously in Scheme A, step i.

If further functionalization is desired, the A$_1$ amine terminus, if A$_1$ is not a bond, or the A$_2$ amine terminus, if A$_1$ is a bond, of the appropriate Boc-A$_1$-A$_2$-A$_3$-A$_4$-A$_5$-A$_6$-Ψ[CH$_2$-N(Q)]-A$_7$[CH$_2$OH] peptide alcohol of structure (25) may be alkylated, dialkylated, acylated, both alkylated and acylated or coupled with 1–3 amino acid residues to give the corresponding amino acid protected mono-(C$_1$–C$_6$ alkyl)-A$_1$-A$_2$-A$_3$-A$_4$-A$_5$-A$_6$-Ψ[CH$_2$-N(Q)]-A$_7$-Ψ[CH$_2$OH] peptide alcohol of Formula I, the corresponding amino acid protected di-(C$_1$–C$_6$ alkyl)-A$_1$-A$_2$-A$_3$-A$_4$-A$_5$-A$_6$-Ψ[CH$_2$-N(Q))-A$_7$[CH$_2$OH] peptide alcohol of Formula I, the corresponding amino acid protected (C$_2$–C$_{10}$ acyl)-A$_1$-A$_2$-A$_3$-A$_4$-A$_5$-A$_6$-Ψ[CH$_2$-N(Q)]-A$_7$[CH$_2$OH] peptide alcohol of Formula I, the corresponding amino acid protected (C$_1$–C$_6$ alkyl)-(C$_2$–C$_{10}$ acyl)-A$_1$-A$_2$-A$_3$-A$_4$-A$_5$-A$_6$-Ψ[CH$_2$-N(Q)]-A$_7$-Ψ[CH$_2$OH] peptide alcohol of Formula I, the corresponding amino acid protected A$_8$-A$_1$-A$_2$-A$_3$-A$_4$-A$_5$-A$_6$-Ψ[CH$_2$-N(Q)]-A$_7$[CH$_2$OH] peptide alcohol of Formula I, the corresponding amino acid protected A$_9$-A$_8$-A$_1$-A$_2$-A$_3$-A$_4$-A$_5$-A$_6$-Ψ[CH$_2$-N(Q)]-A$_7$[CH$_2$OH] peptide alcohol of Formula I, the corresponding amino acid protected A$_{10}$-A$_9$-A$_8$-A$_1$-A$_2$-A$_3$-A$_4$-A$_5$-A$_6$-Ψ[CH$_2$-N(Q)]-A$_7$(CH$_2$OH] peptide alcohol of Formula I, the corresponding A$_8$ amine terminus alkylated, dialkylated, acylated, both alkylated and acylated amino acid protected A$_8$-A$_1$-A$_2$-A$_3$-A$_4$-A$_5$-A$_6$-Ψ[CH$_2$-N(Q)]-A$_7$[CH$_2$OH] peptide alcohol of Formula I, the corresponding A$_9$ amine terminus alkylated, dialkylated, acylated, both alkylated and acylated amino acid protected A$_9$-A$_8$-A$_1$-A$_2$-A$_3$-A$_4$-A$_5$-A$_6$-Ψ[CH$_2$-N(Q) ]-A$_7$[CH$_2$OH] peptide alcohol of Formula I or the corresponding A$_{10}$ amine terminus alkylated, dialkylated, acylated, both alkylated and acylated amino acid protected A$_{10}$-A$_9$-A$_8$-A$_1$-A$_2$-A$_3$-A$_4$-A$_5$-A$_6$-Ψ[CH$_2$-N(Q)]-A$_7$[CH$_2$OH] peptide alcohol of Formula I as described previously in Scheme B, step b. These compounds are then deprotected according to Scheme A, step i.

Starting materials for use in Scheme D are readily available to one of ordinary skill in the art.

The following examples present typical syntheses as described in Scheme D. These examples are understood to be illustrative only and are not intended to limit the scope of the present invention in any way.

EXAMPLE 4--MDL 100,988

Asp-Ser-Phe-Val-Gly-Leu-Ψ[CH$_2$-N(CH$_2$CF$_3$)]-Leu [CH$_2$OH]•trifluoroacetate—SEQ ID NO:21.

Step a: Boc-Leu-Ψ[CH$_2$NH]-Leu[CH$_2$OH]

Dissolve Boc-Leu-Leu(OMe) (3.6 g, 10 mmol) in benzene (60 mL) and cool to 5° C. Add, by dropwise addition, Red-Al (20.5 mL of a 3.4 M solution in toluene, 70 mmol) and reflux for 10 minutes. Cool to room temperature, pour into ice-cold 0.5 M citric acid and adjust to pH 2.5 with citric acid. Wash with ether and adjust to pH 9 with saturated sodium hydrogen carbonate. Saturate with sodium chloride and extract with ethyl ether. Dry (MgSO$_4$), evaporate the solvent in vacuo and purify by silica gel chromatography (5% methyl/methylene chloride) to give the title compound (1.55 g, 49%).

Step b: Boc-Leu-Ψ[CH$_2$-N(CH$_2$CF$_3$)]-Leu(CH$_2$OH]

Dissolve Boc-Leu-Ψ[CH$_2$NH]-Leu[CH$_2$OH] (0.49 g, 1.04 mmol) in anhydrous benzene (1 mL). Add 2,2,2-trifluoroethyl trifluoromethanesulfonate (0.11 g, 0.47 mmol) and stir under a nitrogen atmosphere at 60° C. overnight. Add additional 2,2,2-trifluoroethyl trifluoromethanesulfonate and triethylamine and reflux overnight. Cool to 0° C. and filter. Wash the filtrate with saturated sodium hydrogen carbonate, dry (MgSO$_4$) and evaporate the solvent in vacuo. Purify by silica gel chromatography (chloroform) to give the title compound (0.26 g, 43.5%).

Step c: Leu-Ψ[CH$_2$-N(CH$_2$CF$_3$)]-Leu[CH$_2$OH]•hydrochloride

Mix Boc-Leu-Ψ[CH$_2$-N(CH$_2$CF$_3$)]-Leu[CH$_2$OH] (398 mg, 1 mmol), 4 N hydrochloric acid in dioxane. Stir at room temperature for 30 minutes. Evaporate the solvent in vacuo to give the title compound.

Step d: Boc-Asp(OBn)-Ser(OBn)-Phe-Val-Gly-Leu-Ψ[CH$_2$-N(CH$_2$CF$_3$)]-Leu[CH$_2$OH]—SEQ ID NO:22.

Prepare Boc-Ser(OBn)-Phe-Val-Gly(OMe) by standard solution phase peptide synthesis.

Mix Boc-Ser(OBn)-Phe-Val-Gly(OMe), SEQ ID NO:23, (3.95 g, 6.45 mmol), 1 N sodium hydroxide (39 mL, 39 mmol), methanol (100 mL) and dioxane (60 mL). Stir at room temperature under a nitrogen atmosphere until hydrolysis is complete. Evaporate the solvent in vacuo and purify by silica gel chromatography (chloroform) to give Boc-Ser(OBn)-Phe-Val-Gly, SEQ ID NO:25, (3.32 g, 85.4%).

Mix Boc-Ser(OBn)-Phe-Val-Gly, SEQ ID NO:24, (0.6 g, 1.0 mmol), Leu-Ψ[CH$_2$-N(CH$_2$CF$_3$)]-Leu[CH$_2$OH] hydrochloride (0.3 g, 1.0 mmol), 1-(3-dimethylaminopropyl)-3-ethylcarbodiimide hydrochloride (EDC) (0.22 g, 1.1 mmol), 1-hydroxybenzotriazole hydrate (0.17 g, 1.1 mmol), diisopropylethylamine (0.29 g, 1.1 mmol) and methylene chloride (10 mL). Stir at room temperature under a nitrogen atmosphere until the reaction is complete. Dilute with ethyl acetate and wash with 1 N hydrochloric acid, saturated sodium hydrogen carbonate and brine. Dry (MgSO$_4$) and evaporate the solvent in vacuo to give Boc-Ser(OBn)-Phe-Val-Gly-Leu-Ψ[CH$_2$-N(CH$_2$CF$_3$)]-Leu[CH$_2$OH], SEQ ID NO:25 (0.65 g, 74%).

Mix Boc-Ser(OBn)-Phe-Val-Gly-Leu-Ψ[CH$_2$-N(CH$_2$CF$_3$)]-Leu[CH$_2$OH], SEQ ID NO:25, (0.65 g, 0.74 mmol), 4 N hydrochloric acid in dioxane. Stir at room temperature under a nitrogen atmosphere until hydrolysis is complete. Evaporate the solvent in vacuo to give Ser(OBn)-Phe-Val-Gly-Leu-Ψ[CH$_2$-N(CH$_2$CF$_3$)]-Leu[CH$_2$OH] hydrochloride, SEQ ID NO:26, (0.66 g). Mix Boc-Asp(OBn) (0.26 g, 0.81 mmol), Ser(OBn)-Phe-Val-Gly-Leu-Ψ[CH$_2$-N(CH$_2$CF$_3$)]-Leu[CH$_2$OH] hydrochoride , SEQ ID NO:26, (0.66 g, 0.81 mmol), 1-(3-dimethylaminopropyl)-3-ethylcarbodiimide hydrochloride (EDC) (0.18 g, 0.89 mmol), 1-hydroxybenzotriazole hydrate (0.14 g, 0.89 mmol), diisopropylethylamine (0.23 g, 0.89 mmol) and dimethylformamide (8 mL). Stir at room temperature under a nitrogen atmosphere until the reaction is complete. Dilute with ethyl acetate and wash with 1 N hydrochloric acid, saturated sodium hydrogen carbonate and brine. Dry (MgSO$_4$) and evaporate the solvent in vacuo to give the title compound (0.63 g).

Scheme At step i; Asp-Ser-Phe-Val-Gly-Leu-Ψ[CH$_2$-N(CH$_2$CF$_3$)]-Leu[CH$_2$OH]•trifluoroacetate—SEQ ID NO:21.

Dissolve Boc-Asp(OBn)-Ser(OBn)-Phe-Val-Gly-Leu-Ψ[CH$_2$-N(CH$_2$CF$_3$)]-Leu[CH$_2$OH] (0.63 g, 0.58 mmol) in hydrogen fluoride and anisole. Stir at 0° C. for 1 hour. Allow the solvent to evaporate to give the title compound following HPLC purification.

The following compounds can be prepared in a similar fashion to that described above in Example 4:

Asp-Ser-Phe-Val-⊖-Ala-LeuΨ[CH$_2$-N(CH$_2$CF$_3$)]-Phe [CH$_2$OH]—SEQ ID NO:27; and pyroGlu-Phe-Phe-Gly-LeuΨ[CH$_2$-N(CH$_2$CF$_3$)]-Nle [CH$_2$OH]—SEQ ID NO:28.

The compounds of Formula I wherein A$_7$ is an amino acid residue as previously described wherein the —COOH group is replaced with a —CH$_2$OH group and the reduced amide bond substitution represented by —Ψ[CH$_2$-N(Q)] is located between amino acid residues of A$_1$–A$_2$, wherein A$_1$ is not a bond, A$_2$–A$_3$, A$_3$–A$_4$, A$_4$–A$_5$ or A$_5$–A$_6$ can be prepared by techniques and procedures well known and appreciated by one of ordinary skill in the art. General synthetic procedures for preparing these compounds are set forth in Scheme E. In Scheme E, all substituents unless otherwise indicated are as previously defined.

Scheme E

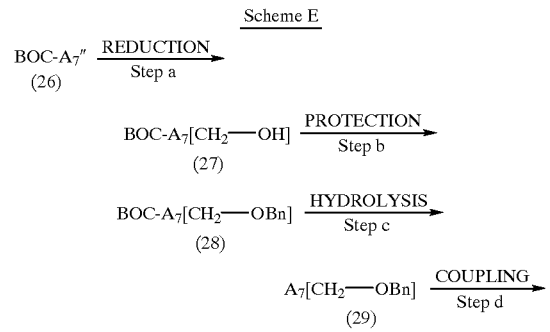

A$_7''$ = A$_7$ as previously defined wherein the ——COOH group is replaced replaced with ——C(O)OCH$_3$ Scheme E provides a general synthetic procedure for preparing the compounds of Formula I wherein A$_7$ is an amino acid residue as previously described wherein the —COOH group is replaced with a —CH$_2$OH and the reduced amide bond substitution represented by —Ψ[CH$_2$-N(Q)] is located between amino acid residues of A$_1$–A$_2$, wherein A$_1$ is not a bond, A$_2$–A$_3$, A$_3$–A$_4$, A$_4$–A$_5$ or A$_5$–A$_6$.

In step a, the methyl ester functionality of the appropriate Boc-A$_7$ amino acid methyl ester of structure (26) is reduced to give the corresponding Boc-A$_7$[CH$_2$OH] amino acid of structure (27) as described previously in Scheme C, step a.

In step b, the hydroxy functionality of the appropriate Boc-A$_7$Ψ[CH$_2$-OH] amino acid of structure (27) is protected as its benzyl ether to give the corresponding BOC-A$_7$[CH$_2$OBn] amino acid of structure (28).

For example, the appropriate Boc-A$_7$[CH$_2$OH] amino acid of structure (27) is contacted with an equimolar amount of benzyl chloride, an equimolar amount of a suitable base such as potassium carbonate and a catalytic amount of a alkylation catalyst, such as sodium iodide. The reactants are typically contacted in a suitable organic solvent such as acetone. The reactants are typically stirred together for a period of time ranging from 2–24 hours at a temperature range of from room temperature to reflux. The Boc-$A_7$[$CH_2OBn$] amino acid of structure (28) is recovered from the reaction zone by extractive methods as is known in the art. It may be purified by chromatography.

In step c, the Boc-protecting group on the $A_7$ amino acid of the appropriate Boc-$A_7$[$CH_2OBn$] amino acid of structure (28) is removed to give the corresponding $A_7$[$CH_2OBn$] amino acid of structure (29) as described previously in Scheme A, step g.

In step d, the appropriate $A_7$[$CH_2OBn$] amino acid of structure (29) is coupled to give the corresponding Boc-protected compounds of Formula I wherein $A_7$ is an amino acid residue as previously described wherein the —COOH group is replaced with a —$CH_2OH$ and the reduced amide bond substitution represented by —Ψ[$CH_2$-N(Q)] is located between amino acid residues of $A_1$–$A_2$, wherein $A_1$ is not a bond, $A_2$–$A_3$, $A_3$–$A_4$, $A_4$–$A_5$ or $A_5$–$A_6$ as described previously in Scheme A, step h.

For example, if the reduced amide bond is located between amino acid residues $A_1$ and $A_2$, wherein $A_1$ is not a bond, the appropriate $A_7$[$CH_2OBn$] amino acid of structure (29) is coupled with Boc-$A_6$ to give the corresponding Boc-$A_6$–$A_7$[$CH_2OBn$] peptide. The Boc-protecting group on amino acid $A_6$ is then removed to give the corresponding $A_6$–$A_7$[$CH_2OBn$] peptide which is then coupled with the appropriate Boc-$A_5$ to give the corresponding Boc-$A_5$-$A_6$-$A_7$[$CH_2OBn$] peptide. The Boc-protecting group on amino acid $A_5$ is then removed to give the corresponding $A_5$-$A_6$-$A_7$[$CH_2OBn$] peptide which is then coupled with the appropriate Boc-$A_4$ to give the corresponding Boc-$A_4$-$A_5$-$A_6$-$A_7$[$CH_2OBn$] peptide. The Boc-protecting group on amino acid $A_4$ is then removed to give the corresponding $A_4$-$A_5$-$A_6$-$A_7$[$CH_2OBn$] peptide which is then coupled with the appropriate Boc-$A_3$ to give the corresponding Boc-$A_3$-$A_4$-$A_5$-$A_6$-$A_7$[$CH_2OBn$] peptide. The Boc-protecting group on amino acid $A_3$ is then removed to give the corresponding $A_3$-$A_4$-$A_5$-$A_6$-$A_7$[$CH_2OBn$] peptide which is then coupled with the appropriate Boc-$A_n$-Ψ[$CH_2$-N(Q)]-$A_{n+1}$ peptide of structure (21), as represented by Boc-A1-Ψ[$CH_2$-N(Q)]-$A_2$, to give the corresponding Boc-$A_1$-Ψ[$CH_2$-N(Q)]-$A_2$-$A_3$-$A_4$-$A_5$-$A_6$-$A_7$[$CH_2OBn$] peptide of Formula I, wherein $A_1$ is not a bond.

If the reduced amide bond is located between amino acid residues $A_2$ and $A_3$, the appropriate $A_4$-$A_5$-$A_6$-$A_7$[$CH_2OBn$] peptide is coupled with the appropriate Boc-$A_n$-Ψ[$CH_2$-N(Q)]-$A_{n+1}$ peptide of structure (21), as represented by Boc-$A_2$-Ψ[$CH_2$-N(Q)]-$A_3$, to give the corresponding Boc-$A_2$-Ψ[$CH_2$-N(Q)]-$A_3$-$A_4$-$A_5$-$A_6$-$A_7$[$CH_2OBn$] peptide. The Boc-protecting group on amino acid $A_2$ is then removed to give the corresponding $A_2$-Ψ[$CH_2$-N(Q)]-$A_3$-$A_4$-$A_5$-$A_6$-$A_7$[$CH_2OBn$] peptide which is then optionally coupled with the appropriate Boc-$A_1$, wherein $A_1$ in not a bond, to give the corresponding $A_1$-$A_2$-Ψ[$CH_2$-N(Q)]-$A_3$-$A_4$-$A_5$-$A_6$-$A_7$[$CH_2OBn$] peptide of Formula I.

If the reduced amide bond is located between amino acid residues $A_3$ and $A_4$, the appropriate $A_5$-$A_6$-$A_7$[$CH_2OBn$] peptide is coupled with the appropriate Boc-$A_n$-Ψ[$CH_2$-N(Q)]-$A_{n+1}$ peptide of structure (21), as represented by Boc-$A_3$-Ψ[$CH_2$-N(Q)]-$A_4$, to give the corresponding Boc-$A_3$-Ψ[$CH_2$-N(Q)]-$A_4$-$A_5$-$A_6$-$A_7$[$CH_2OBn$] peptide. The Boc-protecting group on amino acid $A_3$ is then removed to give the corresponding $A_3$-Ψ[$CH_2$-N(Q)]-$A_4$-$A_5$-$A_6$-$A_7$[$CH_2OBn$] peptide which is then coupled with the appropriate Boc-$A_2$ to give the corresponding Boc-$A_2$-$A_3$-Ψ[$CH_2$-N(Q)]-$A_4$-$A_5$-$A_6$-$A_7$[$CH_2OBn$] peptide. The Boc-protecting group on amino acid $A_2$ is then removed to give the corresponding $A_2$-$A_3$-Ψ[$CH_2$-N(Q)]-$A_4$-$A_5$-$A_6$-$A_7$[$CH_2OBn$] peptide which is then optionally coupled with the appropriate Boc-$A_1$, wherein $A_1$ in not a bond, to give the corresponding Boc-$A_1$-$A_2$-$A_3$-Ψ[$CH_2$-N(Q)]-$A_4$-$A_5$-$A_6$-$A_7$[$CH_2OBn$] peptide of Formula I.

If the reduced amide bond is located between amino acid residues $A_4$ and $A_5$, the appropriate $A_6$-$A_7$[$CH_2OBn$] residue is coupled with the appropriate Boc-$A_n$-Ψ[$CH_2$-N(Q)]-$A_{n+1}$ peptide of structure (21), as represented by Boc-$A_4$-Ψ[$CH_2$-N(Q)]-$A_5$, to give the corresponding Boc-$A_4$-Ψ[$CH_2$-N(Q)]-$A_5$-$A_6$-$A_7$[$CH_2OBn$] peptide. The Boc-protecting group on amino acid $A_4$ is then removed to give the corresponding $A_4$-Ψ[$CH_2$-N(Q)]-$A_5$-$A_6$-$A_7$[$CH_2OBn$] peptide which is then coupled with the appropriate Boc-$A_3$ to give the corresponding Boc-$A_3$-$A_4$-Ψ[$CH_2$-N(Q)]-$A_5$-$A_6$-$A_7$[$CH_2OBn$] peptide. The Boc-protecting group on amino acid $A_3$ is then removed to give the corresponding $A_3$-$A_4$-Ψ[$CH_2$-N(Q)]-$A_5$-$A_6$-$A_7$[$CH_2OBn$] peptide which is then coupled with the appropriate Boc-$A_2$ to give the corresponding Boc-$A_2$-$A_3$-$A_4$-Ψ[$CH_2$-N(Q)]-$A_5$-$A_6$-$A_7$[$CH_2OBn$] peptide. The Boc-protecting group on amino acid $A_2$ is then removed to give the corresponding $A_2$-$A_3$-$A_4$-Ψ[$CH_2$-N(Q)]-$A_5$-$A_6$-$A_7$[$CH_2OBn$] peptide which is then optionally coupled with the appropriate Boc-$A_1$, wherein $A_1$ in not a bond, to give the corresponding Boc-$A_1$-$A_2$-$A_3$-$A_4$-Ψ[$CH_2$-N(Q)]-$A_5$-$A_6$-$A_7$[$CH_2OBn$] peptide of Formula I.

If the reduced amide bond is located between amino acid residues $A_5$ and $A_6$, the appropriate $A_7$[$CH_2OBn$] residue of structure (29) is coupled with the appropriate Boc-$A_n$-Ψ[$CH_2$-N(Q)]-$A_{n+1}$ peptide of structure (21), as represented by Boc-$A_5$-Ψ[$CH_2$-N(Q)]-$A_6$, to give the corresponding Boc-$A_5$-Ψ[$CH_2N(Q)$]-$A_6$-$A_7$[$CH_2OBn$] peptide. The Boc-protecting group on amino acid $A_5$ is then removed to give the corresponding $A_5$-Ψ[$CH_2$-N(Q)]-$A_6$-$A_7$[$CH_2OBn$] peptide which is then coupled with the appropriate Boc-$A_4$ to give the corresponding Boc-$A_4$-$A_5$-Ψ[$CH_2$-N(Q)]-$A_6$-$A_7$[$CH_2OBn$] peptide. The Boc-protecting group on amino acid $A_4$ is then removed to give the corresponding $A_4$-$A_5$-Ψ[$CH_2$-N(Q)]-$A_6$-$A_7$[$CH_2OBn$] peptide which is then coupled with the appropriate Boc-$A_3$ to give the corresponding Boc-$A_3$-$A_4$-$A_5$-Ψ[$CH_2$-N(Q)]-$A_6$-$A_7$[$CH_2OBn$] peptide. The Boc-protecting group on amino acid $A_3$ is then removed to give the corresponding $A_3$-$A_4$-$A_5$-Ψ[$CH_2$-N(Q)]-$A_6$-$A_7$[$CH_2OBn$] peptide which is then coupled with the appropriate Boc-$A_2$ to give the corresponding Boc-$A_2$-$A_3$-$A_4$-$A_5$-Ψ[$CH_2$-N(Q)]-$A_6$-$A_7$[$CH_2OBn$] peptide. The Boc-protecting group on amino acid $A_2$ is then removed to give the corresponding $A_2$-$A_3$-$A_4$-$A_5$-Ψ[$CH_2$-N(Q)]-$A_6$-$A_7$[$CH_2OBn$] peptide which is then optionally coupled with the appropriate Boc-$A_1$, wherein $A_1$ in not a bond, to give the corresponding Boc-$A_1$-$A_2$-$A_3$-$A_4$-$A_5$-Ψ[$CH_2$-N(Q)]-$A_6$-$A_7$[$CH_2OBn$] peptide of Formula I.

If no further functiqnalization is desired, the Boc protecting group on $A_1$, wherein $A_1$ is not a bond, and the Boc protecting group on $A_2$, wherein $A_1$ is a bond, the benzyl protecting group on $A_7$ and various other protecting groups on amino acids $A_1$–$A_7$, wherein $A_1$ is not a bond, and $A_2$–$A_7$, wherein $A_1$ is a bond, of the appropriate protected compounds of Formula I wherein the reduced amide bond is located between amino acid residues $A_1$–$A_2$, wherein $A_1$ is not a bond, $A_2$–$A_3$, $A_3$–$A_4$, $A_4$–$A_5$ or $A_5$–$A_6$ are removed by methods well known in the art to give the corresponding compounds of Formula I wherein the reduced amide bond is loctated between amino acid residues $A_1$–$A_2$, wherein $A_1$ is not a bond, $A_2$–$A_3$, $A_3$–$A_4$, $A_4$–$A_5$ or $A_5$–$A_6$ as described previously in Scheme A, step i.

If further functionalization is desired, the $A_1$ amine terminus, wherein $A_1$ is not a bond, or the $A_2$ amine terminus, wherein $A_1$ is a bond, of the appropriate protected compounds of Formula I wherein the reduced amide bond is loctated between amino acid residues $A_1$–$A_2$, wherein $A_1$ is not a bond, $A_2$–$A_3$, $A_3$–$A_4$, $A_4$–$A_5$ or $A_5$–$A_6$ may be alkylated, dialkylated, acylated, both alkylated and acylated or coupled with 1–3 amino acid residues to give the corresponding amino acid protected mono-($C_1$–$C_6$ alkyl)-compounds of Formula I wherein the reduced amide bond is located between amino acid residues $A_1$–$A_2$, wherein $A_1$ is not a bond, $A_2$–$A_3$, $A_3$–$A_4$, $A_4$–$A_5$ or $A_5$–$A_6$, the corresponding amino acid protected di-($C_1$–$C_6$ alkyl)-compounds of Formula I wherein the reduced amide bond is located between amino acid residues $A_1$–$A_2$, wherein $A_1$ is not a bond, $A_2$–$A_3$, $A_3$–$A_4$, $A_4$–$A_5$ or $A_5$–$A_6$, the corresponding amino acid protected ($C_2$–$C_{10}$ acyl)-compounds of Formula I wherein the reduced amide bond is located between amino acid residues $A_{1-2}$, wherein Al is not a bond, $A_{2-3}$, $A_{3-4}$, $A_{4-5}$ or $A_{5-6}$, the corresponding amino acid protected ($C_1$–$C_6$ alkyl)-($C_2$–$C_{10}$ acyl)-compounds of Formula I wherein the reduced amide bond is located between amino acid residues $A_{1-2}$, wherein $A_1$ is not a bond, $A_{2-3}$, $A_{3-4}$, $A_{4-5}$ or $A_{5-6}$, the corresponding amino acid protected $A_8$-compounds of Formula I wherein the reduced amide bond is located between amino acid residues $A_1$–$A_2$, wherein $A_1$ is not a bond, $A_{2-3}$, $A_{3-4}$, $A_{4-5}$ or $A_5$–$A_6$, the corresponding amino acid protected $A_9$-$A_8$compounds of Formula I wherein the reduced amide bond is located between amino acid residues $A_{1-2}$, wherein $A_1$ is not a bond, $A_{2-3}$, $A_{3-4}$, $A_{4-5}$ or $A_{5-6}$, the corresponding amino acid protected $A_{10}$-$A_9$-$A_8$-compounds of Formula I wherein the reduced amide bond is located between amino acid residues $A_{1-2}$, wherein $A_1$ is not a bond, $A_{2-3}$, $A_{3-4}$, $A_{4-5}$ or $A_5$–$A_6$, the corresponding $A_8$ amine terminus monoalkylated, dialkylated, acylated, both alkylated and acylated $A_8$-compounds of Formula I wherein the reduced amide bond is located between amino acid residues $A_{1-2}$, wherein $A_1$ is not a bond, $A_{2-3}$, $A_{3-4}$, $A_{4-5}$ or $A_{5-6}$, the corresponding $A_9$ amine terminus monoalkylated, dialkylated, acylated, both alkylated and acylated $A_9$-$A_8$-compounds of Formula I wherein the reduced amide bond is located between amino acid residues $A_{1-2}$, wherein $A_1$ is not a bond, $A_{2-3}$, $A_{3-4}$, $A_{4-5}$ or $A_{5-6}$, the corresponding $A_{10}$ amine terminus monoalkylated, dialkylated, acylated, both alkylated and acylated $A_{10}$-$A_9$-$A_8$-compounds of Formula I wherein the reduced amide bond is located between amino acid residues $A_{1-2}$, wherein $A_1$ is not a bond, $A_{2-3}$, $A_{3-4}$, $A_{4-5}$ or $A_{5-6}$ as described previously in Scheme B. These compounds may be deprotected according the procedure in Scheme A, step i.

Starting materials for use in Scheme E are readily available to one of ordinary skill in the art.

The following examples present typical syntheses as described in Scheme E. These example are understood to be illustrative only and are not intended to limit the scope of the present invention in any way.

EXAMPLE 5

Asp-Ser-Ψ[$CH_2$-N($CH_2CH_2F$)]-Phe-Val-Gly-Leu-Leu[$CH_2OH$]—SEQ ID NO:29.

Scheme C Step a: Boc-Ser(OBn)-Phe($OCH_3$)

Mix Boc-Ser(OBn) (5.9 g, 20 mmol), Phe(OMe) hydrochloride (4.32 g, 20 mmol), 1-(3-dimethylaminopropyl)-3-ethylcarbodiimide hydrochloride (EDC) (3.83 g, 20 mmol), 1-hydroxybenzotriazole hydrate (3.06 g, 20 mmol), diisopropylethylamine (3.5 mL, 20 mmol) and methylene chloride (40 mL). Stir at room temperature under a nitrogen atmosphere until the reaction is complete. Dilute with ethyl acetate and wash with 1 N hydrochloric acid, saturated sodium hydrogen carbonate and brine. Dry ($MgSO_4$) and evaporate the solvent in vacuo to give the title compound.

Scheme C, Step b: Boc-Ser(OBn)Ψ[C(S)-$NH_2$]-Phe($OCH_3$)

Mix Boc-Ser(OBn)-Phe($OCH_3$) (456 mg, 1 mmol), 2,4-bis(phenylthio)-1,3-dithio-2,4-diphosphetane-2,4-dithione (0.45 g, 1.1 mmol) and anhydrous tetrahydrofuran (3 mL). Stir at room temperature under a nitrogen atmosphere for 8 hours. Dilute with ethyl acetate and wash with 1 N hydrochloric acid, saturated sodium hydrogen carbonate and brine. Dry ($MgSO_4$) and evaporate the solvent in vacuo to give the title compound.

Scheme C, Step c: Boc-Ser(OBn) [$CH_2$-$NH_2$]-Phe($OCH_3$)

Dissolve Boc-Ser(OBn)Ψ[C(S)-$NH_2$]-Phe($OCH_3$) (472 mg, 1 mmol) in a mixture of 1:1 tetrahydrofuran/methanol (10 mL). Add nickel chloride hexahydrate ($NiCl_2 \cdot 6H_2O$) (1.9 g, 8 mmol) and cool in an ice bath. Add sodium borohydride (0.91 g, 24 mmol) and stir at room temperature under a nitrogen atmosphere for 20 minutes. Filter and evaporate the solvent in vacuo to give the title compound.

Scheme C, Step d; Boc-Ser(OBn)Ψ[$CH_2$-N($CH_2CH_2F$)]-Phe($OCH_3$)

Mix Boc-Ser(OBn)Ψ[$CH_2$-$NH_2$]-Phe($OCH_3$) (192 mg, 0.435 mmol), 2-fluoroethyl p-toluenesulfonate (379 mg, 1.74 mmol), triethylamine (0.06 mL, 0.435 mmol) and benzene (2 mL). Heat at reflux for 7 days, occasionally adding additional 2-fluoroethyl p-toluenesulfonate and triethylamine. Cool to room temperature, wash with 1 N hydrochloric acid then saturated sodium hydrogen carbonate and brine. Dry ($MgSO_4$) and evaporate the solvent in vacuo to give the title compound.

Scheme C, Step e; Boc-Ser(OBn)Ψ[$CH_2$-N($CH_2CH_2F$)]-Phe

Dissolve Boc-Ser(OBn)Ψ[$CH_2$-N($CH_2CH_2F$)]-Phe($OCH_3$) (0.515 g, 1.055 mmol) in ethanol (10 mL) and add 1 N sodium hydroxide (10 mL). Stir at room temperature overnight. Dilute with water and acidify with 1 N hydrochloric acid. Extract into ethyl acetate, dry ($MgSO_4$) and evaporate the solvent in vacuo to give the title compound.

Step a; Boc-Leu[$CH_2OH$]

Dissolve Boc-Leu(OMe) (2.45 g, 10 mmol) in benzene (60 mL) and cool to 5° C. Add, by dropwise addition, Red-Al (20.5 mL of a 3.4 M solution in toluene, 70 mmol) and reflux for 10 minutes. Cool to room temperature, pour into ice-cold 0.5 M citric acid and adjust to pH 2.5 with citric acid. Wash with ether and adjust to pH 9 with saturated sodium hydrogen carbonate. Saturate with sodium chloride and extract with ethyl ether. Dry ($MgSO_4$), evaporate the solvent in vacuo and purify by silica gel chromatography to give the title compound.

Step b: Boc-Leu[$CH_2OBn$]

Mix Boc-Leu[$CH_2OH$](4.8 g, 22 mmol), benzyl chloride (2.8 g, 20 mmol), potassium carbonate (3.04 g, 22 mmol), sodium iodide (1.5 g, 10 mmol) and acetone (60 mL). Heat at reflux for 16 hours, cool to room temperature and remove the solvent in vacuo. Partition between ethyl ether and 6% sodium hydroxide. Separate the organic phase and filter off any undissolved solid from the organic phase. Dry ($MgSO_4$), filter and evaporate the solvent in vacuo to give the title compound.

Step c: Leu[$CH_2OBn$] hydrochloride

Mix Roc-Leu[$CH_2OBn$] (1.09 g, 3.55 mmol), 4 N hydrochloric acid in dioxane. Stir ar room temperature for 1 hour. Evaporate the solvent in vacuo to give the title compound.

Step d; Boc-Asp(O-β-Chxl)-Ser(OBn)-Ψ[CH$_2$-N(CH$_2$CH$_2$F)]-Phe-Val-Gly-Leu-Leu[CH$_2$OBn]—SEQ ID NO:30.

Mix Boc-Leu (4.62 g, 20 mmol), Leu[CH$_2$OBn] hydrochloride (4.88 g, 20 mmol), 1-(3-dimethylaminopropyl)-3-ethylcarbodiimide hydrochloride (EDC) (3.83 g, 20 mmol), 1-hydroxybenzotriazole hydrate (3.06 g, 20 mmol), diisopropylethylamine (3.5 mL, 20 mmol) and methylene chloride (40 mL). Stir at room temperature under a nitrogen atmosphere until the reaction is complete. Dilute with ethyl acetate and wash with 1 N hydrochloric acid, saturated sodium hydrogen carbonate and brine. Dry (MgSO$_4$) and evaporate the solvent in vacuo to give Boc-Leu-Leu[CH$_2$OBn].

Mix Boc-Leu-Leu[CH$_2$CBn] (1.09 g, 2.60 mmol), 4 N hydrochloric acid in dioxane. Stir at room temperature for 1 hour. Evaporate the solvent in vacuo to give Leu-Leu[CH$_2$OBn] hydrochloride.

Mix Boc-Gly (3.5 g, 20 mmol), Leu-Leu[CH$_2$OBn] hydrochloride (7.14 g, 20 mmol), 1-(3-dimethylaminopropyl)-3-ethylcarbodiimide hydrochloride (EDC) (3.83 g, 20 mmol), 1-hydroxybenzotriazole hydrate (3.06 g, 20 mmol), diisopropylethylamine (3.5 mL, 20 mmol) and methylene chloride (40 mL). Stir at room temperature under a nitrogen atmosphere until the reaction is complete. Dilute with ethyl acetate and wash with 1 N hydrochloric acid, saturated sodium hydrogen carbonate and brine. Dry (MgSQ$_4$) and evaporate the solvent in vacuo to give Boc-Gly-Leu-Leu[CH$_2$OBn].

Mix Boc-Gly-Leu-Leu[CH$_2$OBn], (1.09 g, 2.29 mmol), 4 N hydrochloric acid in dioxane. Stir ar room temperature for 1 hour. Evaporate the solvent in vacuo to give Gly-Leu-Leu[CH$_2$OBn] hydrochloride.

Mix Boc-Val (4.34 g, 20 mmol), Gly-Leu-Leu[CH$_2$OBn] hydrochloride, (8.28 g, 20 mmol), 1-(3-dimethylaminopropyl)-3-ethylcarbodiimide hydrochloride (EDC) (3.83 g, 20 mmol), 1-hydroxybenzotriazole hydrate (3.06 g, 20 mmol), diisopropylethylamine (3.5 mL, 20 mmol) and methylene chloride (40 mL). Stir at room temperature under a nitrogen atmosphere until the reaction is complete. Dilute with ethyl acetate and wash with 1 N hydrochloric acid, saturated sodium hydrogen carbonate and brine. Dry (MgSO$_4$) and evaporate the solvent in vacuo to give Boc-Val-Gly-Leu-Leu[CH$_2$OBn]—SEQ ID NO:31.

Mix Boc-Val-Gly-Leu-Leu[CH$_2$OBn], SEQ ID NO:32, (1.09 g, 1.89), 4 N hydrochloric acid in dioxane. Stir at room temperature for 1 hour. Evaporate the solvent in vacuo to give Val-Gly-Leu-Leu[CH$_2$OBn] hydrochloride, SEQ ID NO:32.

Mix Boc-Ser(OBn)Ψ[CH$_2$-N(CH$_2$CH$_2$F)]-Phe (9.48 g, 20 mmol), Val-Gly-Leu-Leu[CH$_2$OBn] hydrochloride, SEQ ID NO:32, (10.26 g, 20 mmol), 1-(3-dimethylaminopropyl)-3-ethylcarbodiimide hydrochloride (EDC) (3.83 g, 20 mmol), 1-hydroxybenzotriazole hydrate (3.06 g, 20 mmol), diisopropylethylamine (3.5 mL, 20 mmol) and methylene chloride (40 mL). Stir at room temperature under a nitrogen atmosphere until the reaction is complete. Dilute with ethyl acetate and wash with 1 N hydrochloric acid, saturated sodium hydrogen carbonate and brine. Dry (MgSO$_4$) and evaporate the solvent in vacuo to give Boc-Ser(OBn)Ψ[CH$_2$-N(CH$_2$CH$_2$F)]-Phe-Val-Gly-Leu-Leu[CH$_2$OBn], SEQ ID NO;33.

Mix Boc-Ser(OBn)Ψ[CH$_2$-N(CH$_2$CH$_2$F)]-Phe-Val-Gly-Leu-Leu[CH$_2$OBn], SEQ ID NO:34, (1.09 g, 1.17 mmol), 4 N hydrochloric acid in dioxane. Stir ar room temperature for 1 hour. Evaporate the solvent in vacuo to give Ser(OBn)Ψ[CH$_2$-N(CH$_2$CH$_2$F) ]-Phe-Val-Gly-Leu-Leu[CH$_2$OBn] hydrochloride, SEQ ID NO:34.

Mix Boc-Asp(O-β-Chxl) (6.3 g, 20 mmol), Ser(OBn)Ψ[CH$_2$-N[CH$_2$CH$_2$F)]-Phe-Val-Gly-Leu-Leu(CH$_2$OBn] hydrochloride, SEQ ID NO:34, (17.38 g, 20 mmol), 1-(3-dimethylaminopropyl)-3-ethylcarbodiimide hydrochloride (EDC) (3.83 g, 20 mmol), 1-hydroxybenzotriazole hydrate (3.06 g, 20 mmol), diisopropylethylamine (3.5 mL, 20 mmol) and methylene chloride (40 mL). Stir at room temperature under a nitrogen atmosphere until the reaction is complete. Dilute with ethyl acetate and wash with 1 N hydrochloric acid, saturated sodium hydrogen carbonate and brine. Dry (MgSO$_4$) and evaporate the solvent in vacuo to give the title compound.

Scheme A, step i: Asp-Ser-Ψ[CH$_2$-N(CH$_2$CH$_2$F)]-Phe-Val-Gly-Leu-Leu[CH$_2$OH]—SEQ ID NO:29.

Dissolve Boc-Asp(O-β-Chxl)-Ser(OBn)-Ψ[CH$_2$-N(CH$_2$CH$_2$F)]-Phe-Val-Gly-Leu-Leu[CH$_2$OBn], SEQ ID NO:35, (113 mg, 0.1 mmol) in hydrogen fluoride and anisole. Stir at 0° C. for 1 hour. All the solvent to evaporate in vacuo to give the title compound.

The following compounds can be prepared in a similar fashion to that described above in Example 5:

Asp-Ser-PheΨ[CH$_2$-N(CH$_2$CF$_2$H)]-Val-β-Ala-Leu-Phe[CH$_2$OH]—SEQ ID NO:36; and pyroGlu-Phe-PheΨ[CH$_2$-N(CH$_2$CH$_2$F)]-Gly-Leu-Met[CH$_2$OH]—SEQ ID NO:37.

The ability of the peptide derivatives of formula I to act as antagonists of neurokinin A can be demonstrated by, for example, the ability of such peptides to compete with iodinated neurokinin A for mammalian neurokinin A (NK2) receptors using the method of Buck, et al., *Science* 226: 987–989 (1984), by the ability of such compounds to stimulate or to inhibit neurokinin A-induced phosphatidylinositol turnover using the method of Bristow, et al., *British J. Pharmacol.* 90: 211–21 (1987), or to antagonize neurokinin A-induced smooth muscle contraction using the method of Dion, et al., *Life Sciences* 41: 2269–2278 (1987).

By virtue of the ability of the peptide derivatives of this invention to act as antagonists of neurokinin A, the compounds are useful as immunosuppressants and in the treatment of arthritis, asthma, pain, inflammation, tumor growth, gastrointestinal hypermotility, Huntington's disease, psychosis, neuritis, neuralgia, headache including migraine, hypertension, urinary incontinence, urticaria, carcinoid syndrome symptoms, influenza, and common cold. Effective doses, whether oral or parenteral, can be readily determined by those of ordinary skill in the art and are those doses which causes antagonism of the neurokinin A (NK2) receptor.

For example, effective doses of the peptides of this invention could be from about 0.5 μg/kg to about 500 mg/kg of the subject body weight per day. The compounds are conveniently administered in unit dosage forms containing from about 1 mg to about 500 mg of the active compound and can be administered in from one to four or more unit dosage forms per day.

Although some of the peptide derivatives may survive passage through the gut following oral administration, applicants prefer non-oral administration, for example, subcutaneous, intravenous, intramuscular or intraperitoneal; administration by depot injection; by implant preparation; or by application to the mucous membranes, such as, that of the nose, throat and bronchial tubes, for example, in an aerosol can containing a peptide derivative of this invention in a spray or dry powder form.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable, or synthetic origin, for example, peanut oil, soybean oil, and mineral oil. In general, water, saline, aqueous dextrose and related sugar solutions, ethanol and glycols such as propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by the Dow-Corning Corporation.

What is claimed is:

1. A peptide derivative of the formula I;

$$X-A_1-A_2-A_3-A_4-A_5-A_6-A_7 \quad \quad I$$

wherein:

X is

Y, wherein Y is hydrogen, an alkyl of from 1–6 carbons, an acyl group of 2–10 carbon atoms, or $B_1$ and $B_2$, wherein $B_1$ and $B_2$ are each independently selected from the group consisting of an alkyl of from 1–6 carbons and an acyl group of from 2–10 carbon atoms, with the proviso that $B_1$ or $B_2$ are not simultaneously the acyl group;

$A_1$ is -Asp-, or a bond;

$A_2$ is -Ser-, or PyroGlu;

$A_3$ is -Phe-;

$A_4$ is -Val-, or Phe;

$A_5$ is -Gly-, or -β-Ala-;

$A_6$ is -Leu-; and $A_7$ is a residue of an amino acid derivative selected from the group consisting of Methioninamide, Norleucinamide, Leucinamide, and Phenylalaninamide.

wherein:

the peptide derivative of Formula I is further characterized by modifying the peptide bond between the amino acid residues of $A_{6-7}$ to a modified peptide bond of

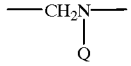

wherein Q is $CH_2CF_3$, $CH_2CHF_2$, $CH_2CH_2F$, or $CH_2CF_2CF_3$, or a pharmaceutically acceptable salt of Formula I with the proviso that when $A_1-A_2$ is selected to be a modified peptide bond, $A_1$ must be -Asp-.

2. The peptide derivative of claim 1 wherein $A_1$ is -Asp-.

3. The peptide derivative of claim 1 wherein $A_2$ is -Ser-.

4. The peptide derivative of claim 1 wherein $A_4$ is -Val-.

5. The peptide derivative of claim 1 wherein $A_5$ is -Gly-.

6. The peptide derivative of claim 1 wherein $A_7$ is a residue of Leucinamide.

7. The peptide derivative of claim 1 wherein X is hydrogen, $A_1$ is -Asp-, $A_2$ is -Ser-, $A_3$ is -Phe-, $A_4$ is -Val-, $A_5$ is -Gly-, $A_6$ is -Leu-, $A_7$ is the residue of Leucinamide, and Q is $CH_2CF_3$·SEQ ID NO:2.

8. The peptide derivative of claim 1 wherein Q is $CH_2CF_3$.

9. A pharmaceutical composition comprising a peptide derivative of formula I of claim 1 and a pharmaceutically acceptable carrier.

10. The peptide derivative of claim 1 wherein Y is hydrogen.

11. The peptide derivative of claim 9 wherein Y is H.

12. A method of treating asthma in a patient in need thereof comprising administering to the patient an effective amount of a peptide derivative of claim 1.

* * * * *